United States Patent [19]

Chan et al.

[11] Patent Number: 5,272,063
[45] Date of Patent: Dec. 21, 1993

[54] PROCESS OF MAKING HUMAN NERVE GROWTH FACTOR

[75] Inventors: Hardy W. Chan, Belmont; Jim W. Barnett, La Honda; Preston A. Baecker, Sunnyvale; Helia Bursztyn-Pettegrew, Palo Alto; Binh T. Nguyen, San Jose; Carol Ward, La Honda, all of Calif.

[73] Assignee: Syntex (U.S.A.) Inc., Palo Alto, Calif.

[21] Appl. No.: 383,118

[22] Filed: Jul. 20, 1989

Related U.S. Application Data

[63] Continuation-in-part of Ser. No. 274,878, Nov. 22, 1988, abandoned.

[51] Int. Cl.$^5$ .................... C12P 21/02; C12N 15/62; C12N 5/10; C12N 15/85
[52] U.S. Cl. ................... 435/69.1; 435/69.7; 435/235.1; 435/320.1; 435/240.2
[58] Field of Search .............. 435/172.3, 235.1, 320.1, 435/69.1, 69.4, 69.7, 69.8, 240.1, 240.2, 948; 935/11, 13, 24, 32, 49, 51, 57, 66, 72

[56] References Cited

U.S. PATENT DOCUMENTS 4,745,051 5/1988 Smith et al. ............... 435/172.3 X
5,082,774 1/1992 Heinrich ........................ 435/69.1

FOREIGN PATENT DOCUMENTS 0121338 10/1984 European Pat. Off. .
0228036 7/1987 European Pat. Off. .
88/02030 3/1988 PCT Int'l Appl. .
89/01028 2/1989 PCT Int'l Appl. .

OTHER PUBLICATIONS

Iwai et al., *Chem. Pharm. Bull.* 34:4724 (1986).
Kang, C. Y., et al., *J. Gen. Virol.* 68:2607 (1987).
Matsuura et al., *J. Gen. Virol.* 68:1233 (1987).
Luckow and Summers, *Biotechnology* 6:47 (1988).
Felgner et al., *Proc. Natl. Acad. Sci.* 84:7413 (1987).
Smith et al., *Proc. Natl. Acad. Sci.* 82:8404 (1985).
Felgner, P. L. et al. 1988. *Chemical Abstracts*, vol. 108, p. 194, Abstract 33038.
Evans, B. A. et al. 1985. *EMBO Journal*, vol. 4, pp. 133-138.
Julius, D., et al. 1984. *Cell*, vol. 37, pp. 1075-1089.
Martin, B. M. et al. 1988. *DNA*, vol. 7, pp. 99-106.
Lebacq-Verheyden, A.-M. et al. 1988. *Molecular and Cellular Biology*, vol. 8, pp. 3129-3135.
Hu, G. L. et al. 1988. *Gene* vol. 70, pp. 57-65.
Hallbook, F. et al. 1988. *Molec. Cell. Biol.* vol. 8, pp. 452-456.
Murhammer, D. W. et al. 1988. *Bio/Technology* vol. 6 pp. 1411-1418.

*Primary Examiner*—Richard A. Schwartz
*Assistant Examiner*—Mary E. Mosher
*Attorney, Agent, or Firm*—Linda J. Nyari; David A. Lowin; Tom M. Moran

[57] ABSTRACT

A method for the construction of recombinant DNA molecules capable of producing biologically active human nerve growth factor (hNGF) in insect cells is disclosed. Expression of the mature protein is achieved using the baculovirus expression system. The biologically active hNGF so produced is potentially of value in the treatment of patients suffering from Alzheimer's Disease and other neurological disorders.

8 Claims, 11 Drawing Sheets

FIG._1

| FIG._1A |
| FIG._1B |
| FIG._1C |

FIG._1A

AGCGCATCGAGTGACTTTGGAGCTGGCCTTATATTTGGATCTCCCGGGCAGCTTTTTGGAAACTCCTAGTGAAC

-187 leu CTC lys AAG  
gly GGT arg CGT  pro CCA val GTG  -180 lys AAA  leu TTA gly GGC ser TCC leu CTG glu GAG val GTG gly GGA his CAC gln CAG his CAT gly GGT val GTT — IVS  met ATG leu CTG cys TGC — m  
= h  
-140 lys AAA  phe TTT ala GCA val GTC gln CAG gly GGG ala GCT gly GGA ala GCT trp TGG his CAT ala GCT gly GGA pro CCC lys AAG leu CTC ser TCA gly GGT val GTT ← IVS  ala GCC leu TTG cys TGT  
A  
ser  
gly GGT ala GCC val GTC  lys AAG ala GCA ala GCA phe TTC tyr TAT thr ACT gly GGC arg CGC ser AGT val GTG ser TCT gly GGG pro CCC asn AAT  
C A A ser  his ser CAT AGC val GTA met ATG ser TCC  
A thr  asp GAC  -130 thr ACT C pro  arg CGC A his  val GTG C ala  glu GAG ← IVS  -120 met ATG  
GA  
gly

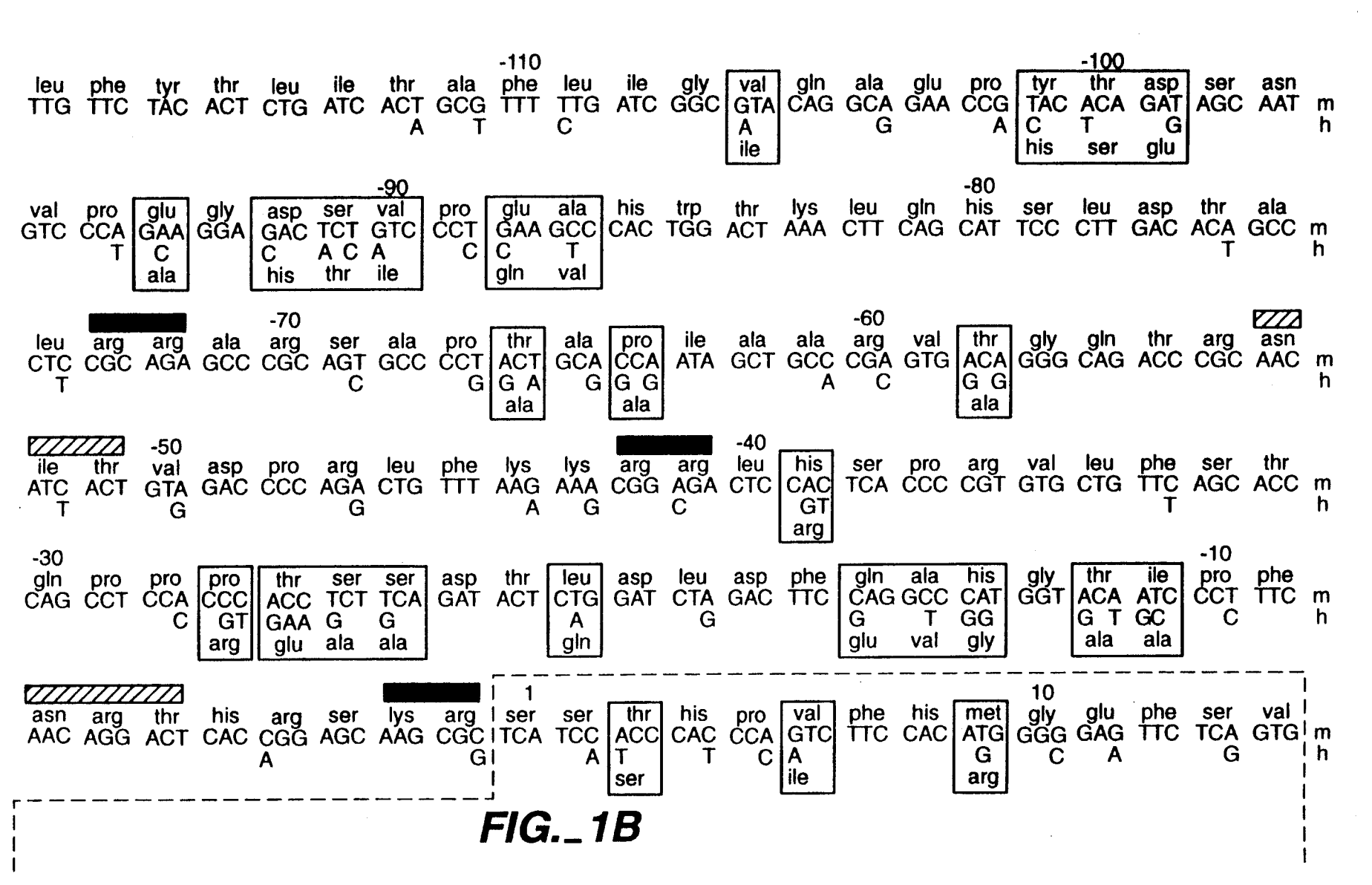

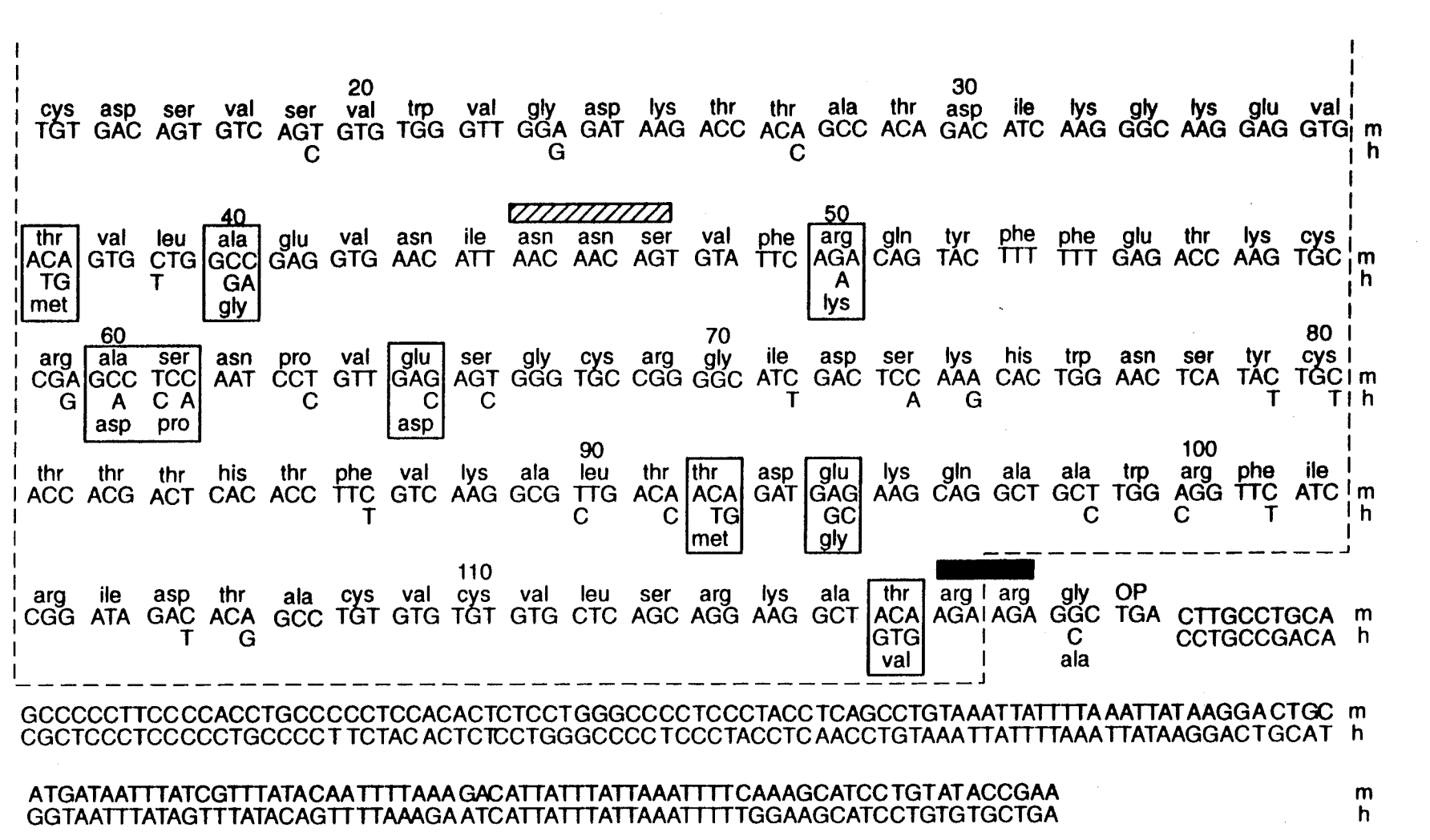

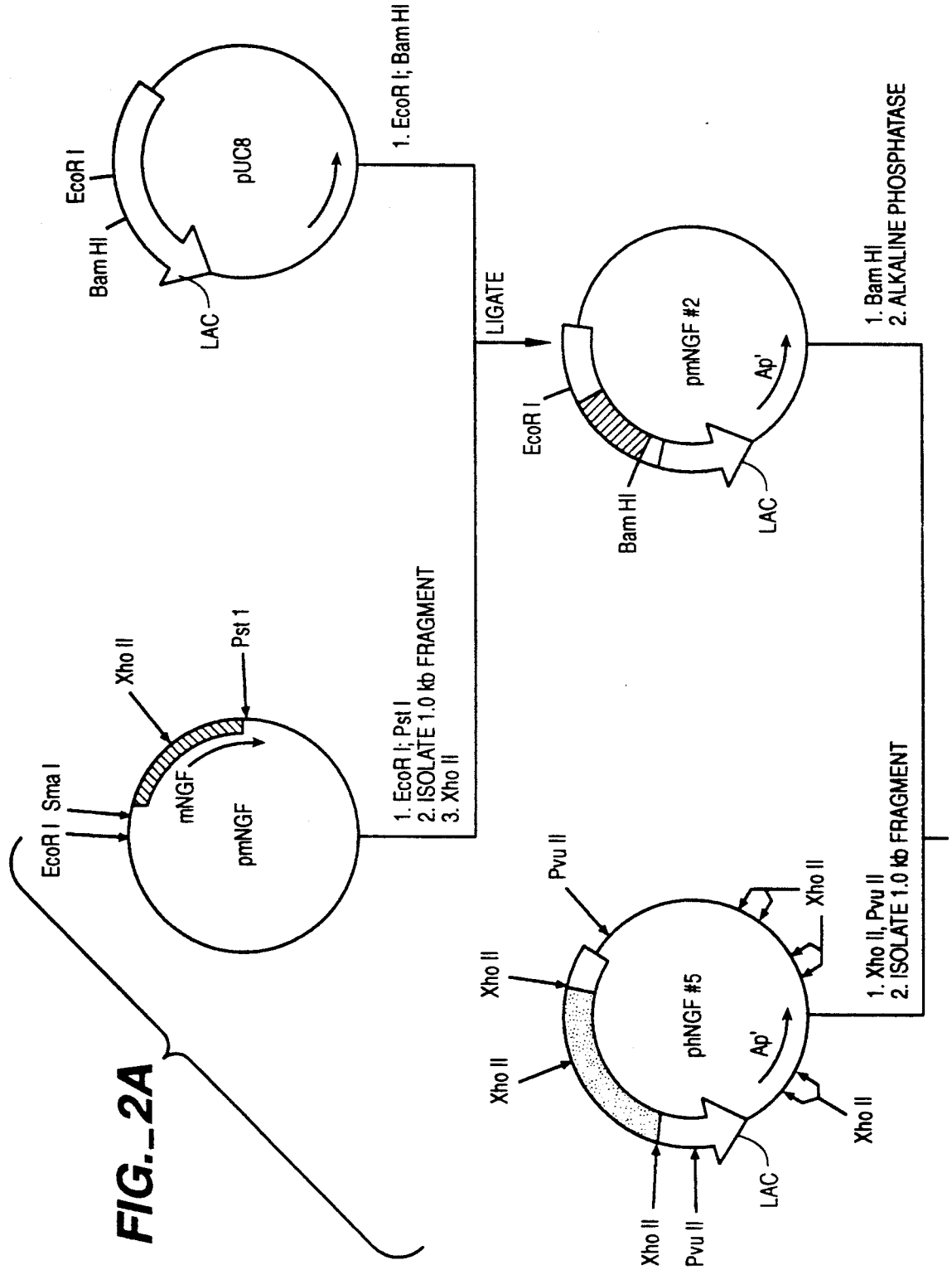

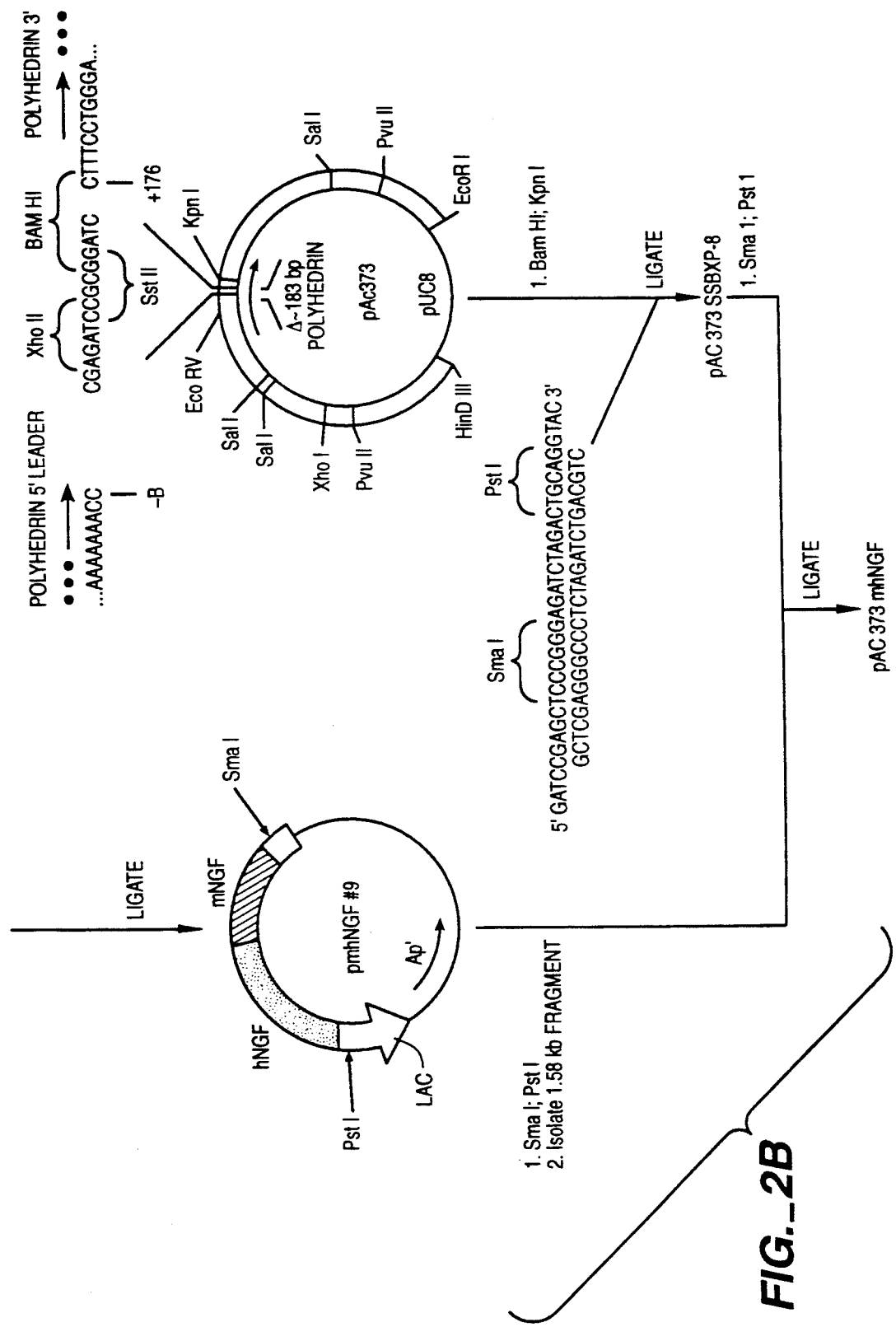
FIG._2B

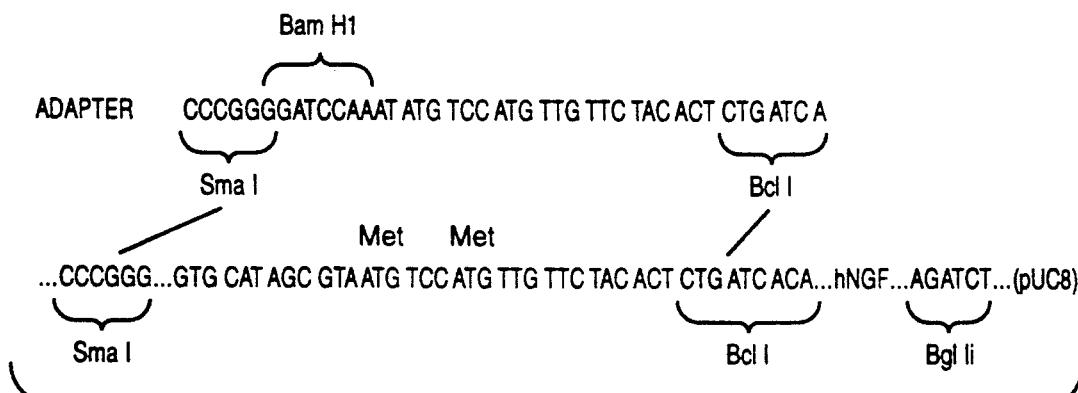
FIG._3A
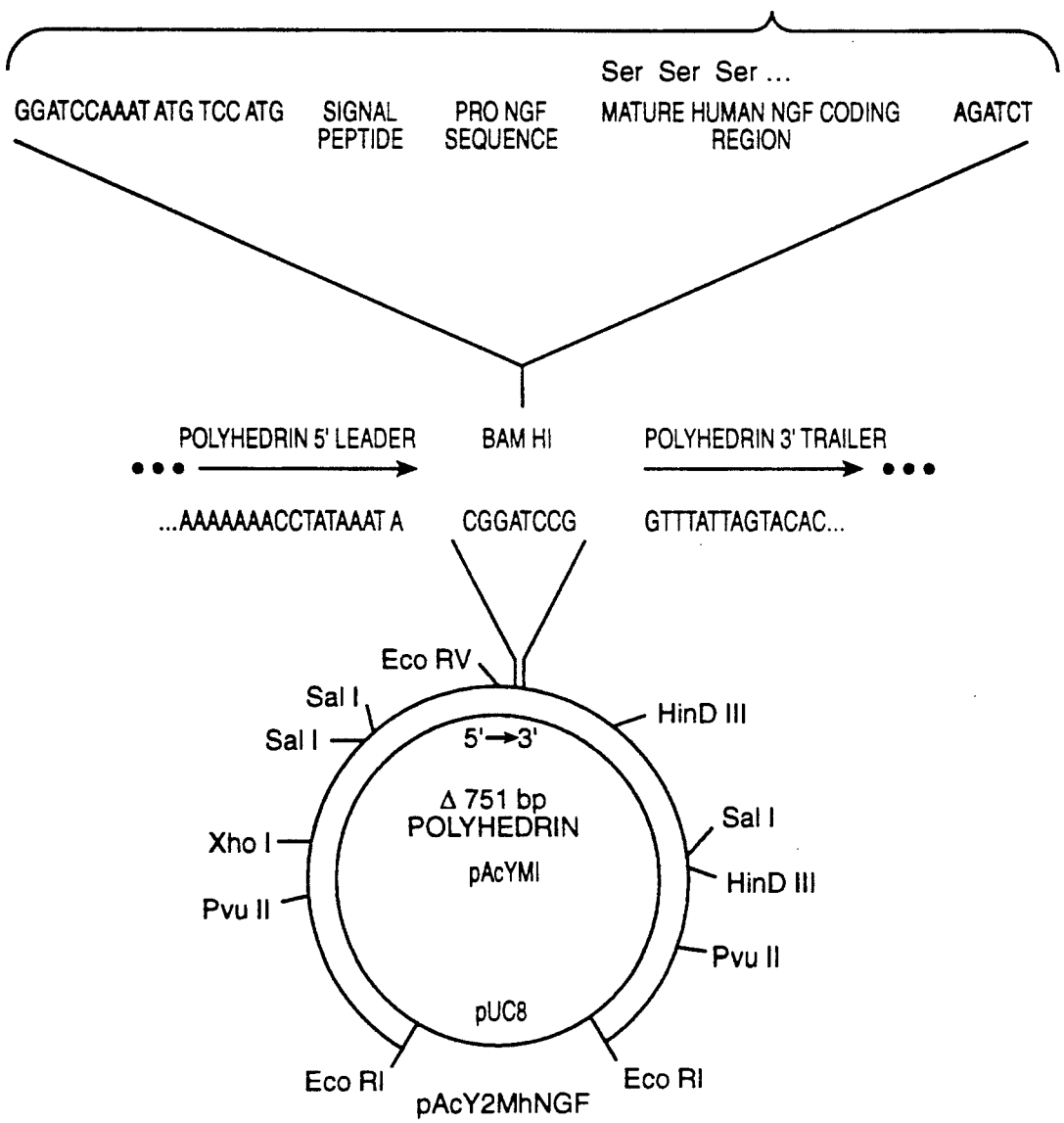
FIG._3B

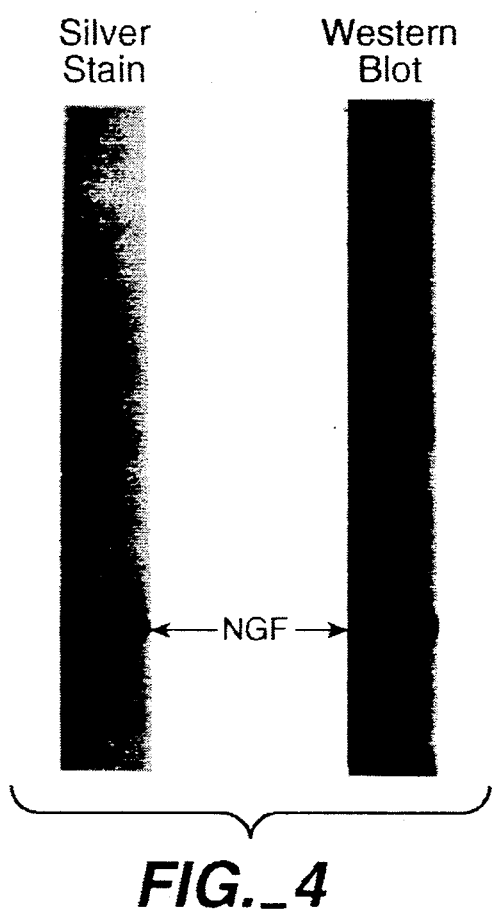
FIG._4

FIG._5A
FIG._5B
FIG._5C
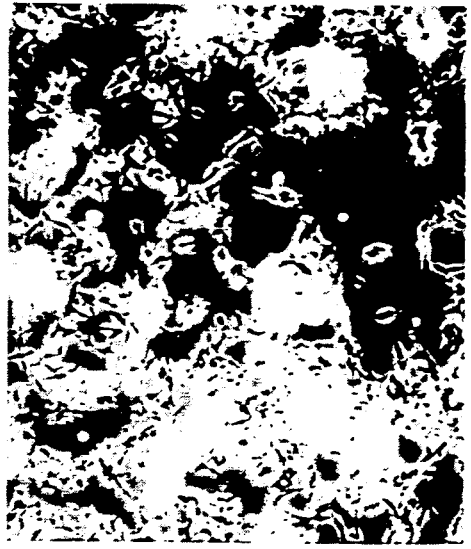
FIG._5D

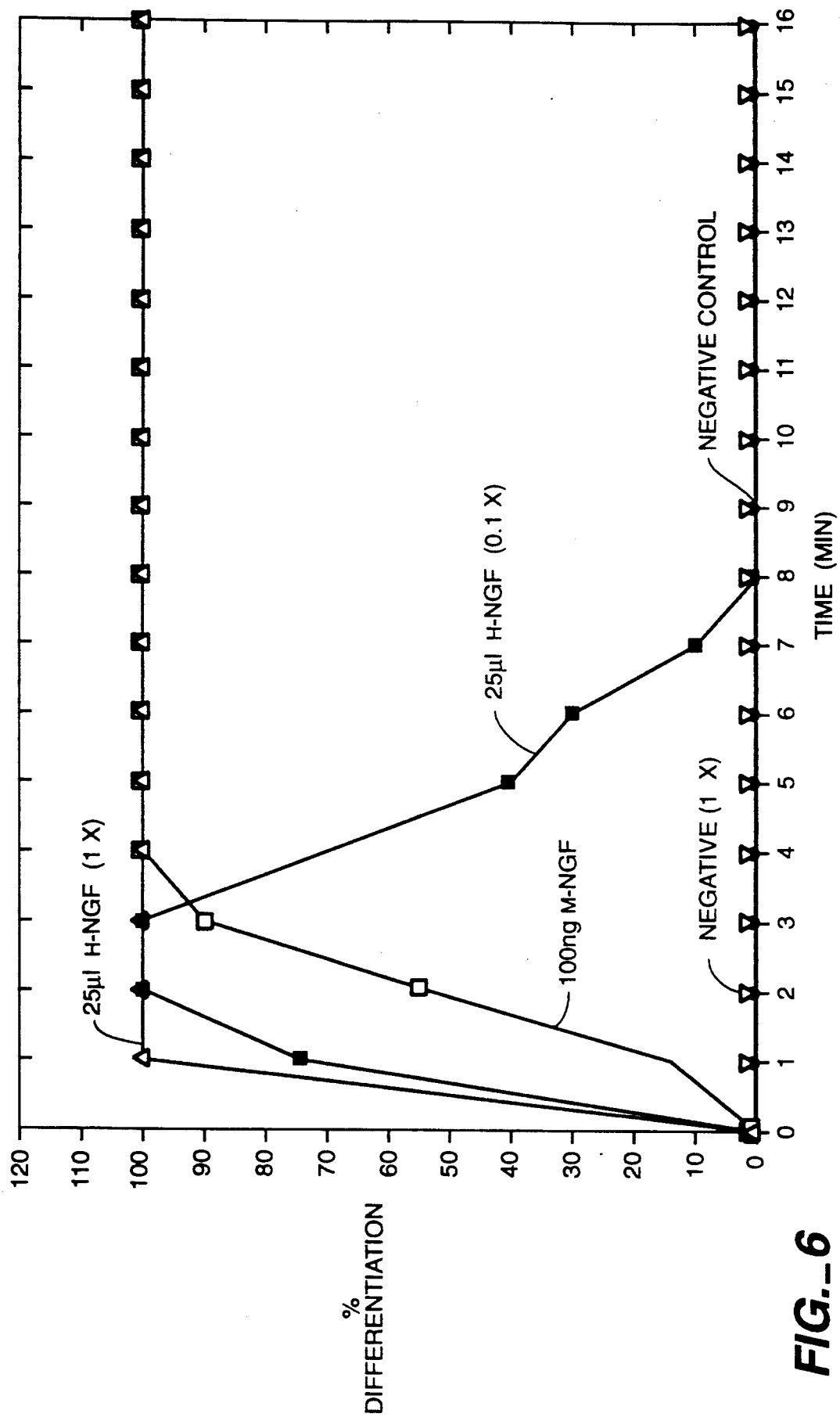
FIG._6

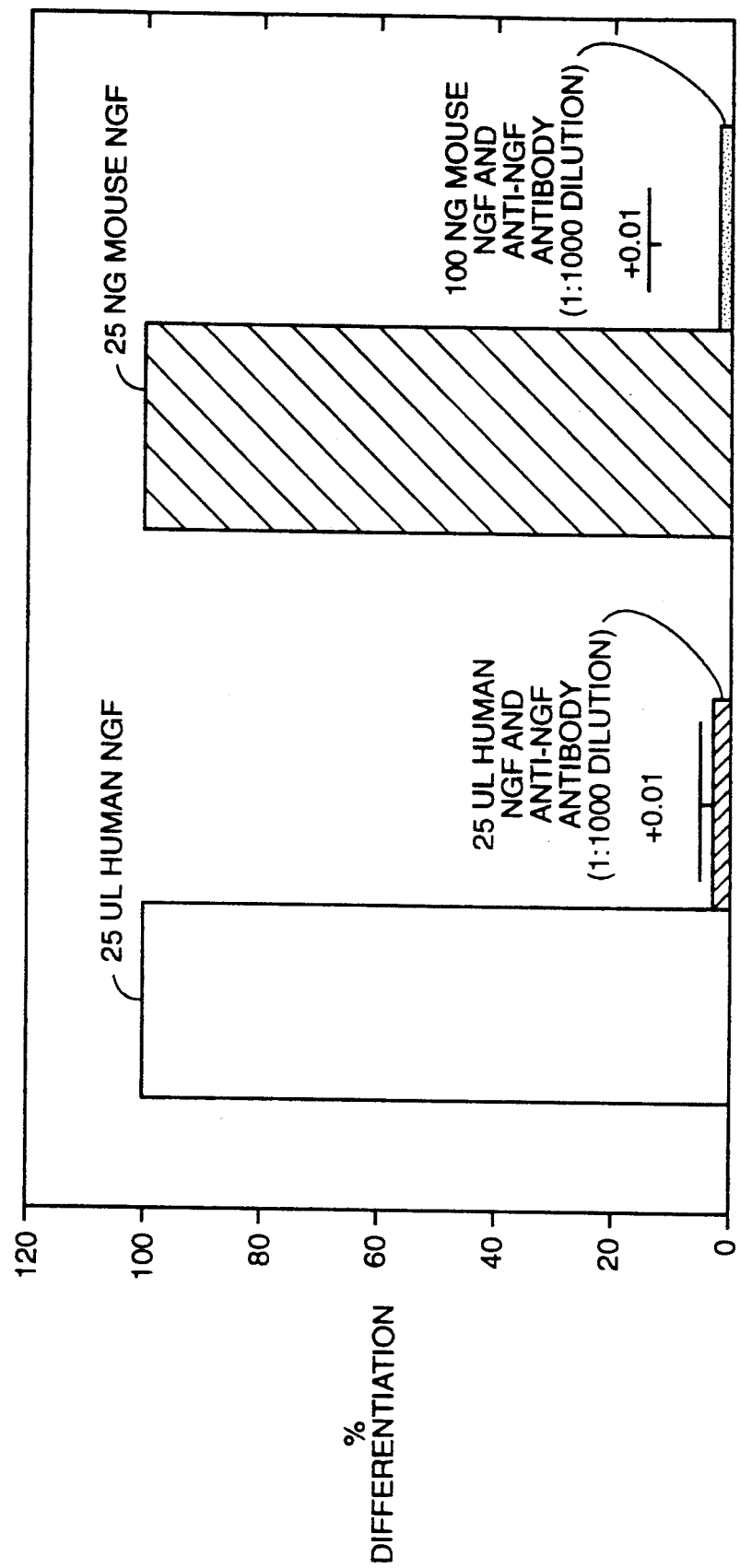
FIG._7

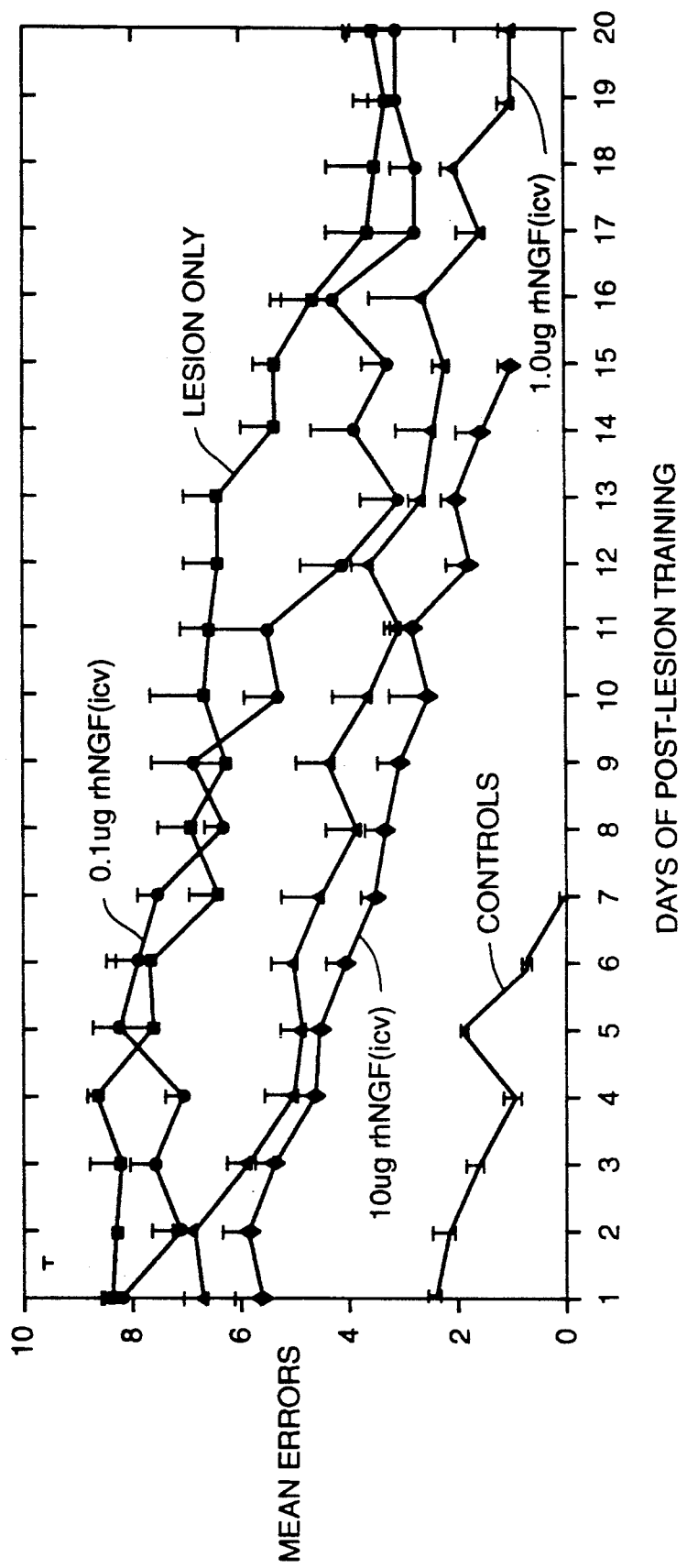
FIG._8

PROCESS OF MAKING HUMAN NERVE GROWTH FACTOR

CROSS-REFERENCE TO RELATED APPLICATIONS

This application is a continuation-in-part of U.S. application Ser. No. 07/274,878, filed Nov. 22, 1988, now abandoned.

FIELD OF THE INVENTION

The present invention relates to the construction of recombinant DNA molecules for the expression of human nerve growth factor (hNGF) by use of a baculovirus expression system. Production of hNGF is achieved using the baculovirus system for expression of the protein in *S. frugiperda* host cells. The recombinant hNGF is of potential use in the treatment of Alzheimer's Disease.

BACKGROUND OF THE INVENTION

The primary structure of a mammalian NGF (mouse NGF) was first elucidated by Angeletti and Bradshaw, *Proc. Natl. Acad. Aci. USA* 68:2417 (1971). The primary structure of its precursor, pre-pro-NGF, has been deduced from the nucleotide sequence of the mouse NGF cDNA (Scott et.al. *Nature* 302:538 (1983); Ullrich et.al. *Nature* 303:821 (1983)).

The highly homologous human NGF (hNGF) gene has also been identified (Ullrich, *Symp. on Quan. Biol., Cold Sprinz Harbor* 48:435 (1983). Its homology to the mouse NGF is 90% and 87%, on the amino acid and nucleotide sequence levels, respectively. Due to the scarcity of hNGF, little is known about its biologic activity.

Baculovirus expression vectors have been used for the expression of a variety of foreign genes in insect cells either or in vivo (See, U.S. Pat. No. 4,745,051, issued May 17, 1988). These expression vectors enlist the highly efficient and temporally regulated *Autographa californica* nuclear polyhedrosis virus (AcNPV) polyhedrin promoter with the gene of interest inserted downstream from the promoter. The corresponding gene product is obtained from *Spodoptera frugiperda* cells infected with the recombinant baculovirus vectors.

The isolation of the β-subunit of hNGF and its expression as a heterologous protein in *E. coli* is described in European Patent Application 0,121,338. By using recombinant techniques, human β-NGF was expressed essentially free from other mammalian proteins. Expression of the hNGF in *E. coli* using two genes which contain altered amino-termini resulting in the expression of a fused protein is described by Iwai, et al., *Chem. Pharm. Bull.* 34:4724 (1986)

The use of recombinant techniques to produce polypeptides in virally infected insect cells is described in European Patent Application 0,228,036. Using the baculovirus expression system, a method for the production of the protein, hepatitis B surface antigen, is set forth. The use of mixed polyhedral inclusion bodies (PIB) which contain a mixture of nucleocapsids from at least two genetically distinct baculoviruses, one of which contains the heterologous gene of interest, is described in Patent Cooperation Treaty (PCT) application WO 88/02030. Using the described coinfection technique a heterologous protein is expressed.

Although expression of these large mammalian proteins is possible, until the present invention there was little information on the successful expression of small molecules, such as hNGF, using a baculovirus expression system. It has also been questionable whether this particular expression system would be suitable for producing small proteins which require post-translational proteolytic cleavage of the protein precursor in order to exhibit biological activity.

We have now unexpectedly found that hNGF may be successfully expressed using a baculovirus insect cell expression system in good yields.

The instant invention describes the construction of expression vectors of use in a baculovirus system capable of expressing hNGF in a biologically active form. Production of sufficient amounts of hNGF by recombinant DNA technology according to this invention makes it possible to ascertain the potential utility of NGF in the treatment of Alzheimer's Disease (AD).

SUMMARY OF THE INVENTION

One embodiment of the invention is a baculovirus transplacement vector having the gene for human nerve growth factor (hNGF) or derivatives thereof joined in proper orientation to regulatory elements functional in insect cells. Suitably, the gene encoding hNGF is a chimeric gene incorporating the leader sequence and promoter of a baculoviral gene.

In another embodiment of the invention, a method for producing biologically active hNGF and derivatives thereof in insect cells is described. The method comprises inserting the gene for hNGF into a baculovirus transplacement vector to form a chimeric gene. The chimeric gene is then incorporated into a baculovirus followed by the infection of insect cells with the recombinant baculovirus. The infected insect cells are grown, preferably in a low or serum free medium, and the biologically active hNGF is harvested from the spent culture media.

In yet another embodiment of the invention, the biologically active hNGF is prepared as a pharmaceutical composition for use in the treatment of Alzheimer's Disease.

BRIEF DESCRIPTION OF FIGURES

FIG. 1: Amino acid sequence of the mature beta subunit of hNGF:

FIG. 1 is comprised of three sheets, identified as FIG. 1A, FIG. 1B, and FIG. 1C. Comparison of cloned mouse pre-pro-NGF cDNA with human sequences published by Ullrich, Symp. on Quant. Biol., Cold Spring Harbor 48:435 (1983) wherein m refers to the mouse sequence, h refers to the human sequence, and IVS refers to the position of intervening sequences in the human gene.

FIG. 2: Construction of pAc373mhNGF plasmids:

FIG. 2 is comprised of two sheets, identified as FIG. 2A and FIG. 2B.

FIGS. 3A-3B: Construction of pAcYMhNGF plasmids:

FIG. 3A shows construction of the adaptor for use in the construction of pAcYMhNGF plasmids;

FIG. 3B shows the construction of plasmid pAcY2MhNGF.

FIG. 4: Silver stain and Western blot analysis of hNGF purified from virus infected cell supernatants FIGS. 5A-5D: $PC_{12}$ cells treated with culture fluid from pAcyYMhNGF recombinant baculovirus infected cells:

FIG. 5A: PC$_{12}$ cells-control;
FIG. 5B: PC$_{12}$ cells-7 days post hNGF treatment;
FIG. 5C: SH-SY5Y cells-control;
FIG. 5D: SH-SY5Y cells-7 days post hNGF treatment.
FIG. 6: Rate of onset as evidenced by neurite outgrowth
FIG. 7: Biological activity attributed to the baculovirus produced hNGF
FIG. 8: Reduction of memory and cognitive impairment in rats with administration of hNGF

DETAILED DESCRIPTION OF THE INVENTION

The present invention describes a means to produce recombinant hNGF, and derivatives thereof, using the baculovirus expression system. By incorporating the DNA coding sequence for hNGF precursor into a baculovirus expression vector, a biologically active hNGF molecule is expressed.

"Derivatives" of hNGF is intended to include molecules differing from hNGF, for example by amino acid additions, deletions or substitutions, in a manner resulting in the molecule having substantially the same activity as hNGF.

Biologically active hNGF can be expressed in a baculovirus system by construction of a chimeric gene consisting of the gene for pre-pro-hNGF linked to the polyhedrin promoter and leader sequence of baculoviral DNA. Examples of plasmids carrying the promoter and leader sequence for baculoviral DNA include pAcYM1 (Bishop, D. H., *J. of Gen. Virol.* 68:1233 (1987)), pAC101 (U.S. Pat. No. 4,745,501), pAc373 (Smith, G. E., *Proc. Natl. Acad. Sci. USA*, 82:8404 (1985)), and pEV51 (Rice, W. C., *J. Virol.* 61:1712 (1987)). In the preferred practice of the invention, the hNGF gene is inserted in plasmid pAcYM1.

The coding sequence for hNGF is available from several sources, for example, through synthesis of the gene using the known DNA sequence or by the use of standard cloning techniques known to those skilled in the art. cDNA clones carrying the hNGF coding sequence can be identified by use of oligonucleotide hybridization probes specifically designed based on the known sequence of hNGF.

Upon obtaining the hNGF coding sequence, the sequence is inserted into a baculovirus cloning vector, such as, pAcYM1. The cloning vector is constructed so as to provide the appropriate regulatory functions required for the efficient transcription, translation and processing of the coding sequence.

In one aspect of the invention, the recombinant DNA molecules which produce hNGF in *S. frugiperda* cells comprise the DNA coding sequence for hNGF precursor inserted into a baculovirus transplacement vector. By "transplacement vector" is meant a plasmid in which the foreign gene of interest can be inserted downstream from the polyhedrin promoter. In addition, the transplacement vector contains sufficient amounts of the polyhedrin gene sequence to enable homologous recombination with the wild type baculovirus genome such that the progeny virus will now contain the foreign gene sequence of interest under the control of the viral polyhedrin promoter.

By utilizing the baculoviral promoter, the mature hNGF precursor is expressed and subsequently processed to mature hNGF. The mature hNGF is then secreted from cells infected with the recombinant virus.

In the preferred practice of the invention, the baculovirus of use in the homologous recombination is *Autographs californica* designated AcNPV. Other baculovirus systems include by way of example insect viruses isolated from *Bombyx mori* and *Heliothis zea*, and the like, more generally those set out in European Patent Publication 0,228,036. The particular baculovirus system used is determined by the type of genetic manipulation to be carried out.

The gene for hNGF is inserted into the baculovirus transplacement vector so as to have available one of the methionine initiation codons. The hNGF gene, as described thus far, (Ullrich, et.al., *Cold Spring Harbor Symposia on Quant. Biol. XLVIII*, p. 435 (1983)) has methionines at positions −121 and −119 that are likely to be utilized as translational initiation codons (position 1 refers to the N-terminal serine residue of mature hNGF, see FIG. 1). In contrast, the mouse submaxillary gland cDNA for NGF, the most thoroughly studied of the nerve growth factors, has a methionine at position −187 in addition to those at positions −121 and −119. It is not clear in man or mouse, which of the codons function as the translational initiation codon.

Studies with mRNA corresponding to the mouse cDNA show that in vitro translation with a wheat germ extract can initiate translation at methionine −187 (Edwards, et al. *J. Biol. Chem.* 263:6810 (1988)). Consistent with this observation, a NGF precursor has been isolated from mouse submaxillary glands (Saboori and Young, *Biochemistry* 25:5565 (1986)) which indicates initiation of translation can occur at methionine −187 in the submaxillary gland. However, it has also been shown that there are at least three different species of NGF mRNA made in the mouse (Selby, et.al. *Mol. and Cellular Biol.* 7:3057 (1987)). This diversity is accounted for by alternative splicing and/or independent initiation from alternative promoters. Since some of the alternative mouse NGF mRNA's lack the methionine codon at −187 it has been inferred that translation can also initiate at methionine −121 or −119 (Selby et.al., supra).

In contrast to the mouse NGF gene, the human NGF gene structure has not been characterized to the same extent. Hence, it is likewise unclear which of the methionine codons is being utilized for translational initiation. We have now found (as illustrated in Example 3) that initiation of translation occurs most efficiently at methionine −121 (designated the 2-MET position) in the baculovirus expression system, while initiation at methionine −119 (designated the 1-MET position) has been shown to occur inefficiently, if at all.

It has also been observed that correct expression and secretion of biologically active hNGF using the baculovirus expression system of this invention requires the presence of the pro-NGF sequence. Attempts to delete the pro-sequence, i.e. splicing the (pre-)signal sequence directly to the mature hNGF sequence, results in no hNGF secretion.

In the preferred practice of the invention, the gene for hNGF is inserted into a transplacement vector to form a chimeric gene. By co-transfecting cells with the transplacement vector containing the foreign gene of interest and wild-type baculovirus genomic DNA, homologous recombination between the virion DNA and the transplacement vector results in a recombinant genome containing the chimeric NGF gene inserted into the baculovirus polyhedrin gene. Viruses containing the recombinant genome are cloned by plaque purification and utilized as the expression vector. Insect cells infected with the expression vector are grown in low or serum-free medium and hNGF is harvested from the spent culture media.

More specifically, the transplacement vectors incorporating the hNGF gene are constructed by modification of the plasmid carrying the hNGF gene. The plasmid is modified so as to incorporate a convenient restriction site both upstream and downstream from the hNGF coding sequence. The modification is achieved through the use of synthetic adaptors. For example, two oligonucleotide adaptors having the desired restriction sites are synthesized. The first adapter: 5'GGGGATCCAAATATGTCCATGTTGTTCTACACTCT 3' and 5'GATCAGAGTGTAGAACAACATGGACATATTTGGATCCCC3', has the BamHI cleavage site immediately up-stream from the first of the two possible initiation codons (the 2-MET position, position −121, see FIG. 1). Whereas, the second adapter: 5'GGGGATCCAAATATGTTGTTCTACACTCT3' and 5'GATCAGAGTGTAGAACAACATATTT-GGATCCCC3', places the restriction site next to the second methionine codon (the 1-MET position, position −119, see FIG. 1). In addition, synthetic linkers, for example 5'pCAGATCTG, are inserted downstream from the hNGF gene in order to incorporate a convenient restriction site.

In another example, a plasmid carrying the hNGF gene can be inserted immediately downstream from the baculovirus polyhedrin gene promoter, thereby utilizing the baculoviral polyhedrin promoter for the initiation of transcription.

In addition to the methods mentioned above which provide the methionine initiation codon, it is also possible to construct a hybrid or chimeric gene where the pre-pro portions of the NGF gene are those of the mouse submaxillary gland cDNA while the portion of the NGF coding for mature NGF is the human NGF gene sequence (FIG. 1). Such a hybrid or chimeric gene potentially allows for initiation of translation at methionine −187 present in the mouse pre-pro-NGF moiety while resulting in the expression of mature hNGF. Such a chimeric gene has been shown to be correctly folded or post-translationally processed. Using the baculovirus expression system such a chimeric gene has yielded biologically active hNGF.

Using the synthetic adaptors mentioned above, the resulting transplacement vectors are constructed so that the gene for hNGF is located next to one of the two available methionine (met) start codons. The modified sequence for hNGF is combined with a suitable baculovirus transplacement vector, for example pacyml, in order to insert the hNGF gene in the proper orientation. The resulting plasmid contains a baculoviral promoter in close proximity to one of the possible NGF methionine initiation codons.

The recombinant baculovirus transplacement vectors so constructed are selected by, for example, screening for restriction enzyme cleavage sites or DNA sequencing techniques known in the art.

As well as the specific vectors illustrated in the Examples, also specifically covered are derivations of these specific vectors. Derivations will include vectors containing modifications not significantly affecting their key role of providing the hNGF gene in expressable form.

Once the hNGF transplacement plasmids are selected, the plasmid containing the chimeric hNGF gene can be co-transfected along with the baculoviral DNA into a suitable insect host cell. Such host cell can be for example, S. frugiperda (suitably cell line Sf9, ATCC No. CRL 1711), Heliothis zea larva, and the like. Transfection is carried out using standard techniques. Such techniques include, for example, viral transfection, DEAE-dextran induced pinocytosis, calcium phosphate precipitation, and most recently lipofection. In a preferred practice of the invention, transfection is carried out using a lipofection technique as described by Felgner, Proc. Natl. Acad. Sci. USA 84:7413 (1987).

Following transfection, the cells are grown in culture media. Suitably after three or four days the spent supernatant is harvested and plaqued on confluent monolayers of host cells. Occlusion negative plaques which are indicative of recombinant viruses are picked and further plaque purified.

For expression, suitable insect host cells, preferably the Sf9 cells, are then infected with the recombinant virus at suitably 0.01 to 10 plaque forming units/cell and subsequently grown on, preferably low or serum free, media. Culture fluid is harvested after suitably 3 to 7 days and standard identification assays, for example, immunoassays such as ELISA and Western blot analysis, or biological assays, such as $PC_{12}$ cell differentiation (Greene, L. A., Trends Neurosci 7:91 (1986)) are performed.

In order to increase proteolytic processing of the pre-pro-NGF precursor, the methods described above may be enhanced by the coinfection of the host cell with other recombinant viruses. For example, the proteolytic processing of pre-pro-hNGF in S. frugiperda can be enhanced by co-infection of the S. frugiperda cells with recombinant viruses containing the genes for the beta subunit of hNGF and gamma subunit of mNGF. Also useful is the coinfection with recombinant viruses containing the beta subunit of hNGF and the yeast KEX 2 genes or recombinant viruses containing the genes for the beta subunit of hNGF and a human kallikrein protease.

The hNGF of the invention can be further purified from the spent culture media. Standard protein purification techniques, for example, ion-exchange chromatography, reverse-phase chromatography, affinity chromatography, size exclusion chromatography, isoelectric focusing, and like, can be employed.

For use as a therapeutic, hNGF may be further purified to obtain pharmaceutical grade hNGF. A pharmaceutical formulation would be such that a dosage unit of hNGF would comprise an effective amount of hNGF in a suitable pharmaceutical carrier in order to be effective in the treatment of Alzheimer's disease (AD) and other neurological disorders.

The pathology of AD, the most common form of dementia, is complex involving many neuronal systems. The most consistent neuropathologic finding in AD brains is a pronounced loss of central cholinergic neurons (Hyman et.al., Science 225:1168-1170 (1984); Pearson et.al., Brain Research 289:395 (1983), Whitehouse et.al., Science 215:1234 (1982)). This loss is related to the severity of dementia (Perry et.al., British Med. Journal 2:1457 (1978)) and correlated quantitatively to the number of neuritic plaques. The cholinergic neuronal deficit appears to be restricted to neurons forming the ascending pathways of the basal forebrain nuclei (medial septum and nucleus basalis) which extend axonal projections to the hippocampus and cortex. These two regions are particularly important for cognitive function (Mann et.al., *J. Neural. Neurosurg. Psychiatry* 49:310 (1986)). The loss of these neurons results in a marked cerebral atrophy in both the cortex and hippocampus and is regarded as a major contributor to the memory deficits characteristic of AD.

Various methods of treatment of AD have been used based on these neurochemical deficits; currently, the most promising being oral physostigmine, an acetylcholinesterase inhibitor. Intravenous administration of physostigmine has been shown to improve cognitive function in some AD patients (Molls et.al., *Am J. Psychiatry* 142:28 (1985), Davis et.al., *New England J. Med.* 308:721 (1983); Christie et al., *Br. J. Psychiatry* 138:46 (1981)), though its clinical use is limited by its short half-life. The use of neurotrophic factors, nerve growth factor (NGF) in particular, to both prevent cholinergic neuronal degeneration and to enhance neuronal regeneration (Hefti, *Ann. Neurol.* 13:109 (1983)) has recently been suggested as a new approach to AD treatment. See also Hefti, *Ann. Neurol.* 20:275 (1986).

The role of NGF was initially ascribed to regulating the development and maintenance of specific functions of the vertebrate peripheral sympathetic and neural crest-derived sensory neurons (Levi-Montalcini and Angeletti, *Physiol. Rev.* 48: 534 (1986)). More recently, it has also been established that NGF has a trophic role on ascending cholinergic neurons in the basal forebrain.

NGF, its RNA transcripts and receptors, are present in high levels in the hippocampus and cortex areas innervated by these forebrain cholinergic neurons (Korching et.al., *EMBO J.* 4:1389 (1985); Riopelle et.al., *Proc. Soc. Neurosci* 11:1056 (1985); Raivich et al., *Neurosci.* 20:23 (1986), Shelton et.al., *Proc. Natl. Acad. Sci. USA* 83:2714 (1986)). Stimulation of NGF receptors on cholinergic neurons results in an increase of choline acetyltransferase (ChAT) activity in the striatum and basal forebrain nuclei (Mobley et.al., *Mol. Brain Res.* 387:53 (1986); *Science* 229:284 (1985)).

Perhaps the most convincing pieces of evidence for NGF having a trophic role on the basal forebrain neurons are: (a) following lesions to the septo-hippocampal pathway in rat, there is a dramatic increase in endogenous NGF (Gasser et.al., *Brain Res.* 376:351 (1986)) and (b) NGF promotes survival of septal cholinergic neurons and abolishes cognitive impairment following fimbrial transection (Gage, et.al., *J. Comp. Neurol.* 269:147 (1986); Hefti, *J. Neurosci.* 6:2155 (1986); Williams et.al., *Proc. Natl. Acad. Sci. USA* 83:9231 (1986)). Based on these observations, it is possible that loss of cholinergic neurons observed in AD may be a consequence of failure of brain target tissue to synthesize sufficient amounts of NGF to maintain these neurons. Alternatively, it may reflect an abnormality in the response of cholinergic neurons to NGF, i.e., receptor abnormality. Even if aberrant NGF responses are not involved in the pathology of AD, NGF may still be useful in slowing or preventing deterioration of cholinergic neurons and/or increasing CHAT activity in remaining neurons.

An effective pharmaceutical composition for treatment of AD may be administered by any of a variety of routines depending on the specific end use. The most suitable route will depend upon the use and the subject involved.

The exact dose and regiment for administration will depend upon the needs of the individual subject being treated and the degree of affliction. The methods of formulation of proteins in order to achieve an effective pharmaceutical composition are known to those skilled in the art.

Preferably, the composition will be a sterile solution administered by continuous infusion intraventricularly into the brain by means of a cannula. The cannula can be linked to a minipump. Such minipumps can be inserted beneath the skin and can hold an extensive reservoir of drug (enough for weeks or even months). Therapy will preferably be for a prolonged period of weeks or months. Effective dosage rates are envisioned in the 0.1 to 100 µg hNGF per day range into the brain, more suitably 2.5–5 µg/day. Conceivably, the composition could alternatively be administered into the spinal cord. Greater doses would likely be needed via this administration route.

The invention is especially advantageous in providing high yields of hNGF, so allowing a proper investigation of its properties. Yields are preferably in the order of up to 5µg/ml, most preferably up to 10µg/ml culture fluid.

The following examples are illustrative and not limiting of the invention. Unless otherwise specified, all enzymes used in the genetic manipulations were obtained from commercial sources and were used substantially in accordance with the manufacturer's instructions. Cloning procedures were carried out substantially as described by Maniatis, et.al., *Molecular Cloning*, Cold Spring Harbor Laboratory, 1982, unless as specifically described herein.

EXAMPLE 1

Isolation of the human beta-nerve growth factor gene

A human leukocyte genomic library (constructed using cloning vector: lambda EMBL-3) was purchased from Clontech Laboratories, Inc. (Palo Alto, Calif.). About $1.5 \times 10^6$ p.f.u. of the recombinant phages were used to infect *E. coli* LE392 cells (Silhavy, T. J. *Experiments with Gene Fusion*. Cold Spring Harbor Laboratory, pg xi–xii, (1984)) at 0.01 multiplicity of infection. After absorption at 37° C. for 20 min., the infected cells were diluted with 0.7% soft agar and plated onto 12 fresh Luria Broth (LB) plates (150 mm). After six hours at 37° C., the plates were removed from the incubator and chilled overnight. The phage lawns were then overlaid sequentially with two pieces of nitrocellulose filters (BA85/20 0.45 mm, Schleicher and Schuell). The nitrocellulose filters were then alkali denatured (15 min with 0.5M NaOH, 1.5M NaCl), neutralized (15 min at 0.5M TrisHCl, pH 8.0 and 1.5M NaCl), washed (15 min with 6 $\times$ SSC(saline,sodium citrate) and baked at 80° C. for 2 hours. Prior to hybridization, the filters were treated with pre-hybridization solution (6$\times$SSC, 0.1% SDS, 5$\times$Denhardt's solution, 1 mM EDTA, 100 mµ/ml salmon sperm DNA, 100 mµ/ml yeast tRNA and 0.05% Na Pyrophosphate) for 16 hours at 65° C. $^{32}$P labelled (by nick-translation, specific activity $3 \times 10^8$ cpm/µg) mouse beta-NGF cDNA (gift from Dr. W. Rutter, *Nature* 302:538 (1983)) were then added to the nitrocellulose filters and hybridization (6$\times$SSC, 0.1% SDS, 2% skim fat milk, 1 mM EDTA, 0.05% Na Pyrophosphate, 100 µg/ml dextran sulfate) was carried out at 65° C. for 16 hours. The filters were then washed twice with 2$\times$SSC, 0.1% SDS, and once with 0.6$\times$SSC 0.1% SDS (10 min each). The filters were air-dried and exposed to X-ray films at −70° C.

Phage plaques which gave positive hybridization signals were picked and subjected to two additional rounds of subcloning and hybridization. During the third round of hybridization, an end labelled synthetic oligonucleotide (28 mer) complementary to the human NGF gene (5'GAGGTGAACATTAACAACAGT-GTATTCA3') was also employed as a hybridization probe. DNAs prepared from the positive phages were characterized by restriction enzyme digestions and Southern blot analysis, using either nick-translated mouse beta-NGF cDNA or the aforementioned synthetic oligonucleotide as probes. Phages which yield hybridizing fragments of the predicted sizes (i.e., 1.8, 5.7 and 4.4 kb for Bgl II, Eco RI and Hind III fragments, respectively) were chosen. The 1.8 kb Bgl II fragment containing the entire coding sequence for the pre-pro human beta-NGF subunit was excised from the phage DNA and transferred into a pUC8 (Bethesda Research Laboratories, Gaithersburg, Md.) plasmid vector (via its compatible BamHI site). The progeny plasmid was designated phNGF#5.

EXAMPLE 2

Preparation of pAC373mhNGF

The construction of pAC373mhNGF was a multi-step procedure (FIG. 2). Briefly, the construction involved the initial assembly of a chimeric NGF gene in the vector pUC 8, where the 5' end of the NGF chimera consisted of a mouse submaxillary gland NGF cDNA and the 3' end of the NGF chimera consisted of a fragment of human genomic DNA coding for the mature sequence of human NGF.

The baculovirus transfection plasmid pAC373 (Smith, G. E., *Proc. Natl. Acad. Sci. USA.* 82:8404 (1985)), which has a unique BamH I site immediately downstream from the polyhedron gene promoter and a unique Kpn I site within a portion of the polyhedrin structural gene, was modified to accept the NGF chimera by ligating an adapter into the Bam HI and Kpn I restriction sites; the adapter contained unique Sma I and Pst I restriction sites. The chimeric mouse/human NGF gene was then excised from the pUCs vector as a Sma I to Pst I fragment and inserted into the modified pAC373 vector via the Sma I and Pst I restriction sites.

A plasmid designated pmNGF was obtained from Dr. Eric Shooter, Dept. of Neurobiology, Stanford University School of Medicine, Stanford, Calif. 94305. Plasmid pmNGF consists of the 961 base pair Sma I to Pst I fragment of the mouse submaxillary gland cDNA encoding the mouse NGF precursor (prepro mouse NGF) described by Scott et al., *Nature* 302: 538 (1983), subcloned into the vector pGEM 1 (Promega, Middleton, Wis.) via the Sma I and Pst I restriction sites.

Ten micrograms of pmNGF were digested with the restriction endonuclease Eco RI (Bethesda Research Laboratories) using conditions recommended by the supplier. The Eco RI cleaved DNA was subsequently cleaved with Pst I (Bethesda Research Laboratories) according to the suppliers recommendations. The digested DNA fragments were resolved by electrophoresis on a 0.7% agarose gel and the approximately 1,000 base pair fragment recovered from the gel by the DEAE nitrocellulose method of Dretzen et al., *Anal. Biochem.* 112: 295 (1981). Approximately 0.5 micrograms of the recovered Eco RI to Pst I fragment was further digested with the restriction endonuclease Xho II (New England Biolabs, Waltham, Mass.) using conditions recommended by the supplier. The digested DNA was phenol extracted, ethanol precipitated, dried and resuspended in sterile distilled water at a concentration of 50 nanograms per microliter.

One half microgram of the plasmid pUCs was digested with BamH I (Bethesda Research Laboratories) using conditions suggested by the supplier. The BamH I cleaved DNA was further cleaved with the restriction endonuclease Eco RI. The cleaved DNA was phenol extracted and ethanol precipitated. The Xho II cleaved Eco RI to Pst I fragment of pmNGF was ligated to the BamH I and Eco RI cleaved pUC8 in a 25 microliter reaction mixture containing 125 nanograms Eco RI and BamH I cleaved pUCs, approximately 125 nanograms Xho II cleaved Eco RI to Pst I fragment of pmNGF, 1.25 micromoles Tris-HCl, pH 7.8, 0.25 micromoles $MgCl_2$, 0.50 micromoles reduced dithiothreitol, 2.5 nanomoles ATP, and 1 unit T4 DNA ligase (Bethesda Research Laboratories). The reaction mixture was incubated at 15° C. for 16 hours.

The ligation mixture was transformed into competent *E. coli* TG 1 host cells (Taylor, J. W. *Nucl. Acids Res.*, 13:8749 (1985)) and plated onto L agar plates (10 gm tryptone, 5 gm yeast extract, 10 gm NaCl, 15 gm bacto-agar per liter) containing 50 micrograms per ml ampicillin, 50 micrograms per ml 5-bromo-4-chloro-3-indolyl beta-D-galactopyranoside, and 0.05 micromoles per ml isopropyl beta-D-thiogalacto-pyranoside. After growth overnight at 37° C., twelve colorless colonies were randomly picked and each innoculated into 1.5 ml of L broth containing 50 micrograms per ml ampicillin. After 5 hours of growth at 37° C. on a platform shaker, mini-lysate DNA was prepared from each culture by the method of Birnboim and Doly, *Nucleic Acids Research* 7: 1513 (1979). After cleavage with Eco RI and BamH I, four of these mini-lysate plasmid DNA preparations yielded the anticipated fragment of approximately 580 base pairs (the Xho II generated DNA end has such a sequence in this case, that, when ligated to a BamH I generated DNA end, regenerates the BamH I site). One of these plasmids, designated pmNGF#2 was used for further construction.

In order to introduce an Xho II fragment of human genomic DNA encoding the mature portion of hNGF into the BamH I site of pmNGF#2, the vector pmNGF#2 was cleaved with BamH I and treated with alkaline phosphatase to prevent self-ligation. One microgram of pmNGF#2 was digested with the restriction endonuclease BamH I. The cleaved DNA was phenol extracted and ethanol precipitated. The dried DNA pellet was then resuspended in ten microliters sterile distilled water. The BamH I cleaved pmNGF#2 DNA was then treated with alkaline phosphatase in a 21 microliter reaction mixture containing one microgram Bam H I cleaved pmNGF#2, 0.315 micromoles sodium borate, pH 10.4, and 1 unit calf intestine alkaline phosphatase (Sigma Chemicals) by incubation at 37° C. for one hour. After one hour, EDTA, pH 8.0, was added to a final concentration of 5 millimolar and the mixture incubated at 68° C. for 15 minutes. The mixture was then phenol extracted, ethanol precipitated, dried and resuspended in sterile distilled water.

Ten micrograms of phNGF#5 (described in Example 1) were digested with the restriction endonuclease Xho II (New England Biolabs) according to conditions recommended by the supplier. Subsequently, the Xho II digested phNGF#5 DNA was digested with Pvu II (Bethesda Research Laboratories) according to the suppliers recommendations. The Xho II fragment derived from the pUC8 vector portion of the plasmid was approximately the same size as the desired 1,004 base pair hNGF genomic DNA derived Xho II fragment. The pUCs derived fragment contained a Pvu II site and was therefore reduced in size relative to the hNGF genomic DNA derived fragment which did not contain a Pvu II site. The digested DNA fragments were resolved by electrophoresis on a 0.7% agarose gel and the approximately 1,000 base pair fragment recovered from the gel by the DEAE nitrocellulose method of Dretzen et al. Anal. Biochem. 112: 295 (1981).

The recovered 1,000 base pair Xho II hNGF genomic DNA fragment was ligated to the BamH I and alkaline phophatased pmNGF#2 in a 20 microliter reaction mixture containing 120 nanograms BamH I cleaved and alkaline phophatased pmNGF#2, 250 nanograms of 1,000 base pair Xho II hNGF genomic DNA, 1 micromole Tris-HCl, pH 7.8, 0.20 micromoles MgCl$_2$, 0.40 micromoles reduced dithiothreitol, 2 nanomoles ATP, and 1 unit T4 DNA ligase. The reaction mixture was incubated at 15° C. for 16 hours.

The 20 microliter ligation mixture was transformed into competent E. coli TG 1 host cells and plated onto L agar plates containing 50 micrograms per ml ampicillin. After growth overnight at 37° C., 170 isolated, randomly selected colonies, were individually streaked onto 82 mm diameter nitrocellulose filters (type BA85, Schleicher and Schuell).

The colony hybridization procedure of Grunstein and Hogness, as described in Maniatis (p. 312-315) was performed using a 28mer synthetic oligodeoxynucleotide 5'GAGGTGAACATTAACAACAGTGTATTCA 3' which is homologous with the human genomic DNA encoding a portion of the mature form of NGF as a probe after $^{32}$p 5' end labelling. Forty-four of the 170 tested colonies, hybridized with the 28mer probe. Twenty-four of the positively hybridizing colonies were individually inoculated into 1.5 ml of L broth containing 50 micrograms per ml ampicillin. After 5 hours of growth at 37° C. on a platform shaker, mini-lysate DNA was prepared from each culture by the method of Birnboim and Doly (supra). After cleavage with Eco RI, three of these mini-lysate plasmid DNA preparations yielded the anticipated fragment of about 700 base pairs. These plasmids were designated pmhNGF#5, pmhNGF#9 and pmhNGF#21.

DNA sequence analysis of plasmid pmhNGF#9 indicated that it had the desired junction between the mouse cDNA and the human genomic DNA. Ten micrograms of plasmid pmhNGF#9 DNA was cleaved with the restriction endonuclease Sma I (Bethesda Research Laboratories) according to conditions recommended by the supplier. After ethanol precipitation and drying in vacuo, the Sma I cleaved DNA was further digested with the restriction endonuclease Pst I (Bethesda Research Laboratories), according to conditions recommended by the supplier. The approximately 1,580 base pair fragment was resolved by electrophoresis on a 0.7% agarose gel, and the DNA recovered by the DEAE-nitrocellulose method of Dretzen et al, Anal. Biochem. 112: 295 (1981).

The polyhedrin promoter containing baculovirus cloning vector plasmid pAC 373, was modified to accept the 1,580 base pair Sma I to Pst I mouse/human chimeric NGF DNA by the insertion of an adapter containing Sma I and Pst I restriction sites between the unique BamH I and Kpn I sites of pAC 373. The synthetic 35mer oligodeoxynucleotide 5'GATCCGAGCTCCCGGGAGATCTAGACTGCAGGTAC 3' (which contains the SmaI, PstI, and other restriction enzyme sites) was resuspended in distilled water at a concentration of 100 picomoles per microliter. Two hundred picomoles of the 35mer was phosphorylated by incubation in a 20 microliter reaction mixture containing in addition to the 35mer, 1.4 micromoles Tris-HCl, pH 7.6, 0.2 micromoles MgCl$_2$, 0.1 micromoles dithiothreitol, 1 nanomole ATP and 7.5 units T4 polynucleotide kinase (Pharmacia), for one hour at 37° C. The enzyme was then inactivated by heating to 65° C. for 10 minutes. The complementary synthetic 27mer oligodeoxynucleotide 5'CTGCAGTCTAGATCTCCCGGGAGCTGG 3' was treated in a similar manner.

A 5 microliter aliquot of each phosphorylation reaction mixture (containing 50 picomoles of each phosphorylated oligodeoxynucleotide) were combined and the self-complementary oligodeoxynucleotide allowed to anneal to each other by incubation at 70° C. for 4 minutes, followed by incubation at 37° C. for 30 minutes and finally 23° C. for 60 minutes.

Three micrograms of plasmid pAC373 was cleaved with the restriction endonuclease Kpn I (Bethesda Research Laboratories). The Kpn I cleaved pAC373 was further cleaved with the restriction endonuclease BamH I. The Kpn I and BamH I cleaved DNA was phenol extracted, ethanol precipitated, dried in vacuo and resuspended in sterile distilled water at a concentration of 120 nanograms per microliter. The cleaved pAC373 vector DNA was then ligated to the annealed oligodeoxynucleotides in a 20 microliter reaction mixture containing 120 nanograms Kpn I and BamH I cleaved pAC 373 DNA, 1.0 picomole annealed oligodeoxynucleotides, 1 micromole Tris-HCl, pH 7.8, 0.2 micromoles MgCl$_2$, 0.4 micromoles reduced dithiothreitol, 2 nanomoles ATP, and 1 unit T4 DNA ligase. The ligation mixture was incubated at 15° C. for 16 hours.

The 20 microliter ligation mixture was then transformed into competent E. coli HB 101 host cells (Maniatis, T., et al., supra) and plated onto LB agar plates containing 50 micrograms per ml ampicillin. After growth overnight at 37° C., 12 colonies were randomly selected and each innoculated into 1.5 ml of L broth containing 50 micrograms per ml ampicillin. After 5 hours of growth at 37° C. on a platform shaker, mini-lysate DNA was prepared from each culture by the method of Birnboim and Doly (supra).

After cleavage with Pst I and Xho I (a unique restriction site within pAC373), a DNA fragment of the anticipated size of approximately 2,000 base pairs was obtained with all but one of the mini-lysate plasmid DNA preparations. All of the plasmids that had acquired a Pst I restriction site were also found to have acquired a Sma I restriction site, as determined by cleavage with Xho I and Sma I. One of these plasmids, designated pAc 373 SSBXP-8 was utilized for the final plasmid construction.

One microgram of plasmid pAC373 SSBXP-8 was digested with the restriction endonuclease Sma I using conditions recommended by the supplier. After ethanol precipitation, the dried Sma I cleaved DNA pellet was resuspended in sterile distilled water and further cleaved with Pst I (Bethesda Research Laboratories) according to the suppliers recommendations. The Sma I and Pst I cleaved pAC373 SSBXP-8 DNA was phenol extracted, ethanol precipitated, and the dried DNA pellet resuspended in sterile distilled water at a concentration of 100 nanograms per microliter. The cleaved pAC 373 SSBXP-8 vector was then ligated to the previously isolated approximately 1,580 base pair Sma I to Pst I fragment of pmhNGF#9 containing the mouse/-human NGF chimera in a 20 microliter reaction mixture containing 100 nanograms Sma I and Pst I cleaved pAC 373 SSBXP-8, 250 nanograms of the approximately 1,580 base pair Sma I to Pst I fragment of pmhNGF#9, 1.0 micromole Tris-HCl, pH 7.8, 0.20 micromoles MgCl2, 0.40 micromoles reduced dithiothreitol, 2.0 nanomoles ATP, and 1 unit T4 DNA ligase. The reaction mixture was incubated at 15° C. for 16 hours.

The ligation mixture was transformed into competent E. coli HB 101 host cells and plated onto L agar plates containing 50 micrograms per ml ampicillin. After growth overnight at 37° C., twelve colonies were randomly picked and each innoculated into 1.5 ml of L broth containing 50 micrograms per ml ampicillin. After 5 hours of growth at 37° C. on a platform shaker, mini-lysate DNA was prepared from each culture by the methods of Birnboim and Doly (supra). After cleavage with Eco RI, two of these mini-lysate plasmid DNA preparations yielded the anticipated 3,400 base pair fragment.

One of these plasmids, designated pAC 373mhNGF, was utilized for co-transfection of Spodoptera frugiperda Sf9 cells with baculovirus genomic DNA in the manner described in Example 4 below. The resultant recombinant virus was used to infect Sf9 insect cells, and then hNGF was expressed, in the manner described in Example 5 below.

EXAMPLE 3

Preparation of pAcYMhNGF plasmids

The construction of pAcYMhNGF plasmids was a multi-step procedure (FIG. 3). Plasmid phNGF#5 (described in Example 1) was first modified to incorporate convenient restriction enzyme sites both upstream and downstream from the beta-NGF coding sequence. To provide an up-stream Bam HI cleavage site, two oligonucleotide adapters were synthesized. The first adapter: 5'GGGGATCCAAATATGTCCATGTTGTT-CTACACTCT 3' and 5'GATCAGAGT-GTAGAACAACATGGACATATTT-GGATCCCC3', has the BamHI cleavage site immediately up-stream from the first of the two possible initiation codons (the 2-MET position, −121). Whereas, the second adapter: 5'GGGGATCCAAATATGTTGTT-CTACACTCT3' and 5'GATCAGAGT-GTAGAACAACATATTTGGATCCCC3', places the restriction site next to the second methionine codon (the 1-MET position, −119).

The 35mer oligodeoxynucleotide 5'GGGGATC-CAAATATGTCCATGTTGTTCTACACTCT 3' was resuspended in distilled water at a concentration of 100 picomoles per microliter. One hundred picomoles of the 35mer was phosphorylated by incubation in a 20 microliter reaction mixture containing 1.4 micromoles Tris-HCl, pH 7.6, 0.2 micromoles MgCl2, 0.1 micromoles dithiothreitol, 1 nanomole ATP and 7.5 units T4 polynucleotide kinase (Pharmacia), for one hour at 37° C. The enzyme was then inactivated by heating to 65° C. for 10 minutes. The 39mer oligodeoxynucleotide 5'GATCAGAGTGTAGAACAACATG-GACATATTTGGATCCCC 3' was treated in a similar manner.

A 5 microliter aliquot of each phosphorylation reaction mixture (containing 25 picomoles of each phosphorylated oligodeoxynucleotide) were combined and the self-complementary oligodeoxynucleotides allowed to anneal to each other by incubation at 70° C. for 4 minutes, followed by incubation at 37° C. for 30 minutes and finally 23° C. for 60 minutes.

Plasmid DNA of phNGF#5 was prepared from the dam− E. coli host GM 48 (dam3−, dcm6, gal, ara, lac, thr, leu, thi, tona, tsx) and 5 micrograms of the DNA cleaved with the restriction endonuclease Bcl I (Boehringer-Mannheim) according to the suppliers recommendations. After ethanol precipitation, the Bcl I cleaved DNA pellet was dried in vacuo. The dried DNA pellet was resuspended in sterile water and cleaved with endonuclease Sma I. The Sma I and Bcl I cleaved phNGF#5 DNA was phenol extracted, ethanol precipitated, dried in ymm and resuspended in sterile distilled water. The cleaved phNGF#5 vector DNA was then ligated to the annealed oligodeoxynucleotides in a 20 microliter reaction mixture containing 100 nanograms (0.038 picomoles) Bcl I and Sma I cleaved phNGF#5 DNA, 2.5 picomoles annealed oligodeoxynucleotides, 1 micromole Tris-HCl, pH 7.8, 0.2 micromoles MgCl2, 0.4 micromoles reduced dithiothreitol, 2 nanomoles ATP, and 1 unite T4 DNA ligase. The ligation mixture was incubated at 15° C. for 16 hours.

The 20 microliter agation mixture was then transformed into competent E. coli GM 48 host cells and plated onto LB agar plates containing 50 micrograms per ml ampicillin. After growth overnight at 37° C., 12 colonies were randomly picked and each innoculated into 1.5 ml of L broth containing 50 micrograms per ml ampicillin. After 5 hours of growth at 37° C. on a platform shaker, mini-lysate DNA was prepared from each culture by the method of Birnboim and Doly (supra). After cleavage with BamH I and Sal I, each of these mini-lysate DNAs yielded the anticipated 1500 base pair fragment. One of these plasmids, designated phNGF2M was subjected to DNA sequencing by the method of Sanger (Proc. Natl. Acad. Sci. USA., 74:5463 (1977)), and found to have the desired sequence.

Plasmid phNGFlM was constructed in an analogous manner using the synthetic oligonucleotides 5' GGGGATCCAAATATGTTGTTCTACACTCT 3' and 5'GATCAGAGTGTAGAACAACATATTT-GGATCCCC 3'. Upon cleavage with BamH I and Sal I, a mini-lysate plasmid preparation of clone phNGFlm yielded the anticipated 1500 base pair fragment.

In order to obtain a BamH I compatible downstream restriction site for cloning into pAcYM1 (supra), a Bgl II linker was introduced between the two Apa I sites downstream of the hNGF DNA. The 8mer oligodeoxynucleotide 5'CAGATCTG 3' was phosphorylated by incubation in a 20 microliter reaction mixture containing 188 picomoles of the 8mer, 1.4 micromoles Tris-HCl, pH 7.6, 0.2 micromoles MgCl2, 0.1 micromoles reduced dithiothreitol, 1 nanomole ATP and 7.5 units T4 polynucleotide kinase (Pharmacia) for one hour at 37° C. The enzyme was inactivated by heating to 65° C. for 10 minutes. 1.6 micrograms of plasmid phNGF2M was digested with the restriction endonuclease Apa I (New England Biolabs) according to conditions suggested by the supplier. After phenol extraction, ethanol precipitation and drying, the Apa I cleaved DNA was resuspended in sterile distilled water at a concentration of 200 nanograms per microliter. The 3' overhangs of the Apa I cleaved DNAs were next removed (blunt-ended) by incubation with Klenow fragment of E. coli DNA polymerase I and all four dNTPs. 1.4 micrograms of Apa I cleaved phNGF2M was incubated in a 25 microliter reaction mixture consisting of the Apa I cleaved DNA, 1.25 micromoles NaCl, 0.25 micromoles Tris-HCl, pH 7.5, 0.25 micromoles $MgCl_2$, 5 nanomoles each of dATP, dGTP, dTTP, and dCTP and 1 unit Klenow fragment of E. coli DNA polymerase I (Bethesda Research Laboratories) at 23° C. for 10 minutes.

After incubation, 0.5 micromoles of EDTA, pH 8.0, were added, the resulting mixture phenol extracted, ethanol precipitated, dried and resuspended at a DNA concentration of 100 nanograms per microliter. The Apa I cleaved and blunt-ended phNGF2M vector DNA was then ligated to the 8mer Bgl II linker in a 20 microliter reaction mixture containing 100 nanograms Apa I cleaved and blunt-ended phNGF2M, 28 picomoles phosphorylated 8mer linker, 1 micromole Tris-HCl, pH 7.8, 0.2 micromoles $MgCl_2$, 0.4 micromoles reduced dithiothreitol, 2 nanomoles ATP, and 1 unit T4 DNA ligase (Bethesda Research Laboratories).

The ligation mixture was incubated at 23° C. for 16 hours. The DNA ligase was then inactivated by incubation at 65° C. for 10 minutes. The ligated DNA was subsequently cleaved with the restriction endonuclease Bgl II (Bethesda Research Laboratories) according to conditions recommended by the supplier. After phenol extraction, ethanol precipitation and drying, the DNA was resuspended in sterile distilled water at a concentration of 10 nanograms per microliter and the DNA religated in a 20 microliter reaction mixture containing 100 nanograms DNA, 1 micromole Tris-HCl, pH 7.8, 0.2 micromoles $MgCl_2$, 0.4 micromoles reduced dithiothreitol, 2 nanomoles ATP, and 1 unit T4 DNA ligase. The ligation mixture was incubated at 23° C. for 16 hours. The 20 microliter ligation mixture was then transformed into competent E. coli HB 101 host cells and plated onto LB agar plates containing 50 micrograms per ml ampicillin.

After growth overnight at 37° C., 6 colonies were randomly picked and each innoculated into 1.5 ml of L broth containing 50 micrograms per ml ampicillin. After 5 hours of growth at 37° C. on a platform shaker, mini-lysate DNA was prepared from each culture by the method of Birnboim and Doly ( ra). After cleavage with BamH I and Bgl II, two of the mini-lysate plasmid DNA preparations from ligation of phNGF2M yielded the anticipated approximately 780 base pair fragment.

Plasmids phNGF1m was constructed in an analogous manner and the 780 base pair BamH I to Bgl II fragment was purified.

About 2 micrograms of plasmid phNGF2M DNA was cleaved with the restriction endonucleases BamH I and Bgl II. The digested DNA fragments were resolved by electrophoresis on a 0.7% agarose gel and the approximately 780 base pair fragment recovered from the gel by the DEAE nitrocellulose method of Dretzen et al., Anal. Biochem. 112: 295. The recovered DNA was resuspended in sterile distilled water at a concentration of 30 nanograms per microliter.

Nine micrograms of the polyhedrin promoter containing baculovirus transplacement plasmid pAcYM1 (Matsuura, Y., J. of Gen. Virol. 68:1233 (1987)) was cleaved with the restriction endonuclease BamH I using conditions recommended by the supplier. After phenol extraction, ethanol precipitation and drying, the BamH I digested pAcYM1 was resuspended in sterile distilled water and treated with alkaline phophatase in a 21 microliter reaction mixture containing nine micrograms BamH I cleaved pAcYM1, 0.315 micromoles sodium borate, pH 10.4, and 1 unit calf intestine alkaline phosphatase (Sigma) by incubation at 37° C. for one hour. After one hour, EDTA, pH 8.0, was added to a final concentration of 5 millimolar and the mixture incubated at 68° C. for 15 minutes. The mixture was then phenol extracted, ethanol precipitated, dried and resuspended in sterile distilled water.

The previously purified approximately 780 base pair BamH I to Bgl II fragment of phNGF2M was then ligated to the BamH I cleaved and alkaline phosphatased pAcYM1 in a 20 microliter reaction mixture containing 100 nanograms BamH I cleaved and phosphatased pAcYM1, 225 nanograms BamH I to Bgl II (780 base pair fragment) of phNGF2m, 1 micromole Tris-HCl, pH 7.8, 0.2 micromoles $MgCl_2$, 0.4 micromoles reduced dithiothreitol, 2 nanomoles ATP, and 1 unit T4 DNA ligase. The ligation mixture was incubated at 15° C. for 16 hours.

The 20 microliter ligation mixture was then transformed into competent E. coli HB 101 host cells and plated onto LB agar plates containing 50 micrograms per ml ampicillin. After growth overnight at 37° C., 12 colonies were randomly picked and each innoculated into 1.5 ml of L broth containing 50 micrograms per ml ampicillin. After 5 hours of growth at 37° C. on a platform shaker, mini-lysate DNA was prepared from each culture by the method of Birnboim and Doly (supra). After cleavage with the restriction endonucleases Pst I and Xho I, two of these mini-lysate plasmid DNA preparations yielded the anticipated number and sizes of restriction fragments. One of these plasmids, designated pAcY2MhNGF was utilized for co-transfection of Spodoptera frugiperda Sf9 cells with baculovirus genomic DNA.

Plasmid pAcY1MhNGF was constructed in an analogous manner from the BamH I to Bgl II fragment of phNGF1M and pAcYM1.

EXAMPLE 4

Preparation of hNGF recombinant baculoviruses pAcY1MhNGF or pAcY2MhNGF DNAs were co-transfected with baculoviral (AcNPV) DNA into Spodoptera frugiperda cells (Sf9) using a lipofection procedure as described by Felgner, (supra).

Various amounts (1 to 10 microgram) of the pAcYM1 derived hNGF plasmids and 1 microgram of the AcNPV DNA (1.5 ml) were mixed with an equal volume of the "DOTMA" lipid solution (Life Science Technology, MD) (66 μg/ml in HEPES-buffered saline). The liposome encapsulated DNAs were then added to Sf9 cells in T-25 flasks and allowed to incubate for 1.5 hrs. 3 ml of fresh media was then added. After 4 hrs, the original media was withdrawn and replenished with fresh media. After 3 or 4 days of incubation at 27° C., the supernatant fluids were harvested and titrated in confluent monolayers of Sf9 cells. Plaques exhibiting no occlusion bodies (as determined by light microscopy) were picked and re-plaqued twice on Sf9 cells to obtain polyhedrin-negative recombinant viruses. High titer virus ($10^7$ to $10^8$ p.f.u./ml) stocks were prepared.

EXAMPLE 5

Immuno-detections of human beta-NGF in the recombinant virus infected cells supernatant Insect cells [(Fall Armyworm Ovary, *Spodoptera frugiperda* (Sf9), ATCC #CRL1711 obtained from American Type Culture Collection (ATCC), Rockville, Md.] in 35 mm tissue culture dishes were infected at a multiplicity of 100 p.f.u./cell, with, separately, either the pAcY1MhNGF or the pAcY2MhNGF derived recombinant virus. After one hour, the infecting viruses were removed and 2 ml of fresh Grace medium (JR Scientific, Woodland, Calif.) (without fetal calf serum) was added. After 72 hrs, the culture supernatant was recovered and concentrated 10 fold. The concentrated material was subjected to either ELISA or Western blot analysis using anti-mouse NGF antibodies. Both Western blot (FIG. 4) and ELISA results indicated that while pAcY1MhNGF produced no detectible amounts of hNGF, pAcY2MhNGF derived recombinant virus secreted into the culture medium approximately 1 microgram/ml of hNGF.

EXAMPLE 6

Production of hNGF in serum free medium

Serum free medium (XL-400) was purchased from JR Scientific Inc., Woodland, Calif. Sf9 cells propagated in XL-400 medium at 27° C., were grown in suspension in 100 ml shaker flasks. Cell density was maintained at $3 \times 10^5$ to $1 \times 10^6$ cells/ml by diluting with fresh medium. Doubling time in logarithmic phase was approximately 24 hours. Sf9 cells at cell density of $5 \times 10^5$ to $2.4 \times 10^6$ cells/ml were infected with recombinant viruses at various multiplicities of infection (MOI) (from 0.01 to 10 p.f.u./cell).

Culture supernatants were harvested on day 3, 5 and 6 post-infection. After filtering through a 0.22 μm membrane filter system (Corning glassware, Corning, N.Y.), the amount of hNGF present in the filtrate was determined by an ELISA method. In XL-400 medium, recombinant hNGF was optimally produced (approximately 6 μg/ml) 3 days post-infection when Sf9 cells were infected at a density of $2.4 \times 10^6$ cells/ml and a MOI of 0.01.

EXAMPLE 7

Analysis by ELISA

Immulon-2 flat bottom 96 wells plates (Dynatech Labs Inc., Cat. No. 011-010-3450) were coated with anti-mouse-beta (2.5S) NGF (Boehringer Mannheim, Cat. No. 1008218) at a concentration of 0.1 μg/ml and 0.15 ml/well for at least two hours. (NGF was diluted with coating buffer ($Na_2CO_3$/$NaHCO_3$, 50 mM; Na Azide, 0.1% w/v; pH 9.6)). The plates were then washed with washing buffer (50 mM Tris-HCl, pH 7.0; 200 mM NaCl, 10 mM $CaCl_2$, 0.1% (w/v) Triton X-100, 0.05% (w/v) Na-Azide). The plates were next blocked with BSA (1% BSA, Sigma, RIA grade, cat-#A-7888 in washing buffer) for at least 30 minutes at room temperature, and washed again with washing buffer.

A standard curve is included in each of the commercial assays: 2.5 S mouse NGF (Sigma, product No. N6009) previously reconstituted in distilled water at a concentration of 100 μg/ml and stored in 5 μl/tube aliquots at −60° C., was thawed and diluted with 495 μl of sample buffer (blocking buffer supplemented with 20 μg/ml of aprotinin, United States Biochemical Co., Cat. No. 11388). This standard (final NGF concentration at 1 μg/ml) is stable for at least 10 days at 4° C.

The mNGF standard was diluted two fold serially with sample buffer and added onto the ELISA plates (0.1 ml/well; in duplicates). Culture fluid was also diluted serially in sample buffer (¼ to 1/64,000) and added onto the plates (also at 0.1 ml/well). After overnight incubation at 4° C., the wells were washed repeatedly. NGF (2.5S) -beta-gal conjugate (Boehringer Mannheim, Cat. No. 1008234, 0.0125 Units/ml in blocking buffer) was added to each well. After incubation for 4 hours at 37° C., the plates were again washed. 0.2 ml of a freshly prepared substrate solution (2 mg/ml of chlorophenol red-beta-D-galactopyranoside in substrate buffer: 100 mM hepes, pH 7.0; 150 mM NaCl, 2 mM $MgCl_2$; 0.1% (w/v) NaAzide, 1% (w/v) albumin) was added to each of the wells and allowed to incubate for an additional 2 hours at 37° C. The ELISA plates were then read with a Titertek Multiskan microtiter plate reader using a Multiskan interference filter at 570 nm.

EXAMPLE 8

Biologic activity of the baculovirus produced hNGF

The biologic activity of the material produced by recombinant pAcY1MhNGF or pAcY2MhNGF virus was tested in vitro on the $PC_{12}$ pheochromocytoma cell line (Greene L. A., *Trends Neurosci* 7:91 (1986)). $PC_{12}$ cells were grown in Dulbecco's modified Eagle's medium (DMEM) supplemented with 5% defined-supplemented calf bovine serum and 5% horse serum and seeded at a density of about 50,000 cells per well (16 mm). Cells were treated with a single addition of either culture fluids from recombinant baculovirus infected cells, or mouse NGF (Sigma). Cells were observed for up to 14 days post-addition.

$PC_{12}$ cells treated with culture fluid (25 μl/ml media) from pAcY2MhNGF recombinant baculovirus infected cells underwent rapid differentiation (FIG. 5). The rate of onset as evidenced by neurite outgrowth, was substantially more rapid (within 12 hrs) than mouse NGF at 25 and 100 ng per ml media (24–36 hrs) (FIG. 6). The ability to induce rapid differentiation of $PC_{12}$ cells appears to be an intrinsic property of the baculovirus produced hNGF. Duration of differentiation, on the other hand, is concentration dependent. $PC_{12}$ cells treated with a concentrated preparation of infected Sf9 cell fluid, remained differentiated for the duration of the experiment (14 days). Whereas, $PC_{12}$ cells treated with a more dilute preparation (0.1 X) of the baculovirus produced hNGF, reversed their differentiated phenotype after 5 days.

Interestingly, $PC_{12}$ cells treated with pAcY1MhNGF recombinant virus infected cell supernatant, showed no sign of differentiation. This observation is consistent with the negative Western blotting and ELISA results (Example 5).

Biological activity attributed to the baculovirus produced hNGF can be neutralized by an anti-mouse NGF antibody (FIG. 7).

EXAMPLE 9

Neutralization of NGF-Induced Differentiation of $PC_{12}$ Cells $PC_{12}$ cells were plated as described in Example 8 with the following modification: prior to addition of NGF to the culture media, anti-mouse NGF antiserum (Collaborative Research Inc., at 1:500 and 1:1000 dilution of neat serum) was added to the $PC_{12}$ cells. Mouse NGF (Sigma) or recombinant human NGF were then added to the PC$_{12}$ cell cultures and their effect on cell differentiation was observed for a period of 14 days.

NGF induced differentiation of PC$_{12}$ cells by both human (25 μl culture fluid) and mouse (100 ng) NGF was neutralized by anti NGF antiserum at dilutions of 1:500 and 1:1000 neat serum.

EXAMPLE 10

Biological Activity of hNGF on Human Neuroblastoma SH-SY5Y Cells

Cultures of SH-SY5Y cells (Biedler et al., *Cancer Res.* 33: 2643 (1973), ibid, 38:3751 (1978)) were maintained in 75 cm$^2$ Corning T-75 flasks in a 1:1 mixture of Dulbecco's modified Eagles' medium (DMEM) and Ham's F-12 (JR Scientific, Woodland, Calif.) supplemented with 10% fetal bovine serum (JR Scientific) at 37° C. Cells were detached for passaging and harvesting by adding 4 mls of 0.02% EDTA in DMEM per flask followed by vigorous shaking. Cells were passed at a 1:5 split ratio. No antibiotics were used in the cultures at any time. Following exposure of cells to negative control supernatant, NGF (2.5 S mouse NGF, Sigma) at a concentration of 100 ng/ml or human NGF (25 μl/ml), the cells were observed every 24 hours for signs of differentiation. The media was changed every 2 days for the duration of the culture and the NGF replenished. Aphidicolin was added to the medium during the second week of treatment at 10 μg/ml.

Addition of hNGF (25 μl/ml) to SH-SY5Y human neuroblastoma cell line induced rapid differentiation (extension of neurites from cells), though no effect was observed following administration of negative control culture fluid supernatant to SH-SY5Y cells (25 μl/ml). The rapid onset of differentiation due to NGF beginning as early as 24 hours was in contrast to the much slower onset of differentiation observed following addition of mouse NGF (Sigma) to the same cell line (5 days) (Jensen, *Dev. Biol.* 120:56 (1987)).

Aphidicolin has no effect on differentiated cells, but is a reversible inhibitor of alpha DNA polymerase and will therefore kill mitotically dividing cells. It is necessary to treat the cells with aphidicolin in the second week as the few mitotically active cells which were not induced to differentiate by NGF will overgrow the quiescent, i.e., differentiated cells.

EXAMPLE 11

Infection with Recombinant Viruses Containing hNGF gene and Another Gene Coding for a Processing Enzyme in the Same Baculovirus The development of transplacement vectors that are specifically designed to allow high level co-expression of the hNGF gene and another gene coding for a processing enzyme, such as the gamma subunit of NGF or the yeast KEX2 endopeptidase, is an alternative approach to produce high amounts of mature NGF. This can be achieved by inserting the beta-NGF gene downstream from the polyhedrin promoter and either the gamma NGF or the KEX2 gene under the control of a second copy of the polyhedrin promoter, another baculovirus promoter, such as the p10 late promoter or a designed synthetic promoter. Recombinant virus is then generated as described in EXAMPLE 4 and used to infect Sf9 cells as described in EXAMPLE 5.

EXAMPLE 12 hNGF in Impaired Memory Test

General

In this test, the lesions attempt to mimic cholinergic dysfunction in terms of impairment of memory and cognative ability found in AD patients. hNGF treatment significantly reduced the degree of impairment.

Methods

Male Charles River Wistar rats (280–300 g) were housed individually in quarters controlled for sound, temperature and humidity and maintained on a 12 hour light/dark cycle. For the first ten days of study animals had ad lib access to food. From the eleventh day onward, the animals' food supply was reduced until all animals reached 80% of their initial body weight. This weight was maintained throughout training.

Apparatus—A Y-maze was used to pretrain animals, each goal arm measured 13 cm high×13 cm wide×47 cm long. These arms were separated from the approach alley (13 cm high×13 cm wide×40 cm long) by a guillotine door.

Training Procedure—The training and testing procedure essentially followed that of Ramirez and Stein, *Behav. Brain Res.* 13:53 (1982). Briefly, animals were randomly allocated to different experimental groups (n=5–9) and allowed a three-day pretraining period to become familiar with the experimenter and the Y-maze. Animals were then given five days of random alternation training. After placing the rat in the base of the approach alley, the animal was released and allowed to move into one of the arms. Once in the goal arm, the animal received a food reward (45 mg Noyes food pellet). After eating the pellet, the animal was returned to the approach alley, released and allowed to move into the next randomly chosen goal arm, where again the rat received a food reward. The animals were put through a series of ten left/right random alternations in total. Following this forced training period, animals were trained to alternate freely in the maze until all had reached a certain criterion level: three consecutive days of 80% correct alternation behavior.

Surgery—Rats were anesthetized with xylazine (Haver)/ketamine (Parke-Davis) 200:20 mg/kg i.m. and placed in the stereotaxic frame (Kopf Instruments). The skull was exposed, cleaned and two holes were drilled above each of the nucleus basalis of Meynert (NBM) (coordinates were measured from Bregma according to Paxino and Watson, *The Rat Brain in Stereotaxic Coordinates*, 2nd Edition, Academic Press, New York (1986), rostral/caudal −0.4 mm, lateral ± 2.6 mm). The dura beneath the holes were pierced and the tip of a Hamilton syringe, prefilled with ibotenic acid (5 mg/ml), was lowered −6.5 mm and −7.5 mm ventral to the dura. 1.0 μl of ibotenic acid was infused into the NBM over a period of 1 minute.

In addition, a third hole was drilled in the skull it above the lateral ventricles (rostral/caudal −0.8 mm, lateral 1.4 mm) and a stainless steel cannula implanted 4 mm down from the dura into the ventricles. The cannulae were fabricated from 23 g stainless steel needles and were connected to a prefilled, sterile Alzet (Alza, Palo Alto, Calif.) model 2 ml mini-osmotic pump (flow rate 2.4 μl/hr) via polyethylene tubing. The pumps were placed subdermally between the shoulder blades. The wound was then sutured and the animals allowed to recover. Mini-pumps were filled, according to different treatment groups with:

a) hNGF dissolved to a final concentration of 0.1, 1.0 or 10.0 μg/ml in sterile saline containing 0.1 μg/ml rat serum, i.e., rats received 0.2, 2.0 or 20.0 μg hNGF per 4 week treatment period; or b) Saline containing 0.1 mg/ml rat serum.

Procedure

The experimental groups comprised control animals (n=6), lesion only (n=9), lesion with 0.1 μg/ml hNGF (n=9), lesion with 1.0 μg/ml hNGF (n=9) and lesion with 10.0 μg/ml hNGF (n=9). The animals were trained in the spatial alternation task, surgically treated and then allowed a 3 week treatment period. Following this treatment period, the rats were retested in the Y-maze and their behavioral performance evaluated over a period of 20 days.

Statistical analysis—A Cochran-Mantel-Haenszel test was used to obtain tests of significance for overall effects of treatment as well as pairwise differences between treatments.

Results

The mortality rate after lesions in the experimental groups was 40%, the final group numbers were control (6), lesion only (6), lesion with 0.1 μg/ml hNGF (5), lesion with 1.0 μg/ml hNGF (6) and lesion with 10.0 μg/ml hNGF (6).

To determine the effects of ibotenic acid lesions and hNGF on spatial alternation behavior, three behavioral criterion were examined: (i) number of days to reach post-lesion criterion, (ii) mean number of alternation errors per day, and (iii) mean number of perseverative errors per day.

As shown in FIG. 8, bilateral ibotenic acid lesion animals took significantly longer ($p<0.01$) to reach the established criterion level when compared to control animals. This effect was partially ameliorated by hNGF treatment at doses of 1.0 and 10.0 μg/ml. There was a significant difference between lesion only animals and those lesioned but treated with 1.0 μg/ml hNGF ($p <0.01$) and 10.0 μg/ml hNGF ($p <0.01$). There was no significant difference between lesion alone rats and those with lesion but receiving 0.1 μg/ml hNGF.

Bilateral lesions also caused rats to incur significantly more daily alternation errors ($p <0.01$) (see FIG. 8) when compared to control rats and to incur significantly more perseverative errors ($p <0.01$) than control animals.

hNGF treatment limited the extent of the impairments observed following bilateral ibotenic acid lesion to the NBM. There was a significant difference in mean numbers of alternation errors (see FIG. 8) and mean number of perseverative errors between lesion treated and lesion-hNGF treated animals at the 1.0 μg/ml ($p <0.01$) and the 10.0 μg/ml ($p <0.01$) doses. There was no significant difference in mean number of alternation (see FIG. 8) and perseverative errors between lesion treated and lesion 0.1 μg/ml hNGF treated animals up to day 9, however, on day 10 and onwards, there was a significant difference ($p <0.01$) between these groups.

In summary, bilateral ibotenic acid lesions of the nucleus basalis of Meynert in rats significantly impairs learned spatial alternation behavior. This impairment is significantly ameliorated by recombinant hNGF, suggesting that rhNGF ameliorates central cholinergic dysfunction.

The above description and examples fully disclose the invention including preferred embodiments thereof. Modifications of the methods described herein that are obvious to those of ordinary skill in the art of molecular genetics and related sciences are intended to be within the scope of the following claims.

What is claimed is:

1. A method of producing biologically active mature human β-nerve growth factor in insect cells which comprises:

(a) constructing a transplacement vector having an mRNA leader sequence and promoter of a baculovirus polyhedrin gene operatively linked to a DNA coding sequence, said DNA coding sequence consisting of:
        a DNA coding sequence for the pre-pro portion of mouse nerve growth factor; and
        a DNA coding sequence for mature human β nerve growth factor;

(b) incorporating the transplacement vector of (a) into a baculovirus to form a recombinant baculovirus;

(c) infecting insect cells with the recombinant baculovirus of (b);

(d) growing the infected insect cells of (c) in serum free media; and (e) harvesting the human β-nerve growth factor from the media.

2. The method of claim 1 wherein the transplacement vector is pAC373mhNGF.

3. A baculovirus transplacement vector having an mRNA leader sequence and promoter of a baculovirus polyhedrin gene operatively linked to a DNA coding sequence, said DNA coding sequence consisting of:
    a DNA coding sequence for the pre-pro-portion of mouse nerve growth factor; and
    a DNA coding sequence for mature human β-nerve growth factor.

4. The transplacement vector of claim 3 wherein a Bam HI restriction site is inserted upstream from the first methionine initiation codon position from the 5' end of the DNA sequence of pre-pro mouse nerve growth factor.

5. The transplacement vector of claim 4 wherein the synthetic adaptor has the coding sequence:

35 mer: 5'GATCCGAGCTCCCGGGAGATC-TAGACTGCAGGTAC 3'
    27 mer: 5'CTGCAGTCTAGATCTCCCG-GGAGCTGG 3'

6. The transplacement vector of claim 4 which is pAC373mhNGF.

7. An insect cell infected with the transplacement vector of claim 4.

8. The insect cell of claim 7 which is *Spodoptera frugiperda* (Sf9).

* * * * *